(12) United States Patent
Johnson et al.

(10) Patent No.: US 11,031,124 B2
(45) Date of Patent: Jun. 8, 2021

(54) OPTIMIZING STATE TRANSITION SET POINTS FOR SCHEDULE RISK MANAGEMENT

(71) Applicant: General Electric Company, Schenectady, NY (US)

(72) Inventors: Christopher Donald Johnson, Niskayuna, NY (US); Onur Ilkin Dulgeroglu, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 219 days.

(21) Appl. No.: 16/245,919

(22) Filed: Jan. 11, 2019

(65) Prior Publication Data

US 2019/0148008 A1 May 16, 2019

Related U.S. Application Data

(63) Continuation of application No. 14/473,707, filed on Aug. 29, 2014, now Pat. No. 10,217,528.

(51) Int. Cl.
*G16H 40/20* (2018.01)
*G06Q 10/06* (2012.01)

(52) U.S. Cl.
CPC .......... *G16H 40/20* (2018.01); *G06Q 10/0635* (2013.01)

(58) Field of Classification Search
CPC .......................... G16H 40/20; G06Q 10/0635
(Continued)

(56) References Cited

U.S. PATENT DOCUMENTS

| | | | |
|---|---|---|---|
| 2007/0106599 A1* | 5/2007 | Hochberg | G06Q 40/025 705/38 |
| 2009/0089092 A1* | 4/2009 | Johnson | G06F 19/00 705/2 |

(Continued)

OTHER PUBLICATIONS

United States Patent and Trademark Office, "Non-Final Office action" issued in connection with U.S. Appl. No. 14/473,707, dated May 19, 2017, 18 pages.

(Continued)

*Primary Examiner* — Michael Tomaszewski
(74) *Attorney, Agent, or Firm* — Hanley, Flight & Zimmerman, LLC.

(57) ABSTRACT

Systems, methods, and apparatus to dynamically manage interdependent, variable scheduled procedures are provided. An example method includes calculating a cumulative distribution function (CDF) for task(s) in a healthcare protocol based on a probability density function associated with task duration(s) for the task(s). The method includes determining a plurality of schedule risk states for each task in a healthcare protocol, each schedule risk state associated with an upper specification limit (USL) and a lower specification limit (LSL) along the CDF. The method includes identifying, within USL and LSL for each schedule risk state, setpoint(s) associated with probability(-ies) along the CDF. The method includes monitoring execution of task(s) in the healthcare protocol to identify a transition in schedule risk state according to USL and LSL. The method includes triggering an action to react to an actual or upcoming change in schedule risk state based on setpoint(s) associated with the schedule risk state.

20 Claims, 20 Drawing Sheets

(58) Field of Classification Search
USPC .......................................................... 705/2–3
See application file for complete search history.

(56) References Cited

U.S. PATENT DOCUMENTS

| | | | |
|---|---|---|---|
| 2009/0119126 A1* | 5/2009 | Johnson | G06Q 10/063116 |
| | | | 705/2 |
| 2009/0222275 A1* | 9/2009 | Cantor | G06Q 10/30 |
| | | | 705/308 |
| 2011/0270644 A1* | 11/2011 | Roncolato | G06Q 10/0635 |
| | | | 705/7.22 |
| 2016/0063192 A1 | 3/2016 | Johnson et al. | |
| 2019/0148008 A1* | 5/2019 | Johnson | G06Q 10/0635 |
| | | | 705/2 |

OTHER PUBLICATIONS

United States Patent and Trademark Office, "Final Office action" issued in connection with U.S. Appl. No. 14/473,707, dated Dec. 1, 2017, 24 pages.

United States Patent and Trademark Office, "Non-Final Office action" issued in connection with U.S. Appl. No. 14/473,707, dated Mar. 22, 2018, 12 pages.

United States Patent and Trademark Office, "Notice of Allowance" issued in connection with U.S. Appl. No. 14/473,707, dated Oct. 3, 2018, 39 pages.

* cited by examiner

FIG. 5

| | A | B | C |
|---|---|---|---|
| 1 | | MON | TUE |
| 16 | Room: S1 | OrthoGr1:Anes1:AN:Block=1:Serv 9 Hrs(5) | Surgeon2:Anes1:AN:Block=1:Serv 9 Hrs (5) |
| 17 | | OrthoGr1:STech1:ST:Block=1:Serv 9 Hrs(5) | Surgeon2:STech1:ST:Block=1:Serv 9 Hrs (5) |
| 18 | | OrthoGr1:CNurse1:CN:Block=1:Serv 9 Hrs(5) | Surgeon2:CNurse1:CN:Block=1:Serv 9 Hrs (5) |
| 19 | | OrthoGr1:Anes1:AN:Block=2:Serv 9 Hrs(5) | OrthoGr1:Anes1:AN:Block=2:Serv 9 Hrs (5) |
| 20 | | OrthoGr1:STech1:ST:Block=2:Serv 9 Hrs(5) | OrthoGr1:STech1:ST:Block=2:Serv 9 Hrs (5) |
| 21 | | OrthoGr1:CNurse1:CN:Block=2:Serv 9 Hrs(5) | OrthoGr1:CNurse1:CN:Block=2:Serv 9 Hrs (5) |
| 23 | Room: S10 | ThoracicGr1:CNurse6:CN:Block=1:Serv 16 Hrs(5) | OrganTransGr1:Anes2:AN:Block=1:Serv 13 Hrs(5) |
| 24 | | ThoracicGr1:Anes3:AN:Block=1:Serv 16 Hrs(5) | OrganTransGr1:CNurse2:CN:Block=1:Serv 13 Hrs(5) |
| 25 | | ThoracicGr1:STech6:ST:Block=1:Serv 16 Hrs(5) | OrganTransGr1:STech2:ST:Block=1:Serv 13 Hrs(5) |
| 26 | | ThoracicGr1:CNurse6:CN:Block=2:Serv 16 Hrs(5) | OrganTransGr1:Anes2:AN:Block=2:Serv 13 Hrs(5) |
| 27 | | ThoracicGr1:Anes3:AN:Block=2:Serv 16 Hrs(5) | OrganTransGr1:CNurse2:CN:Block=2:Serv 13 Hrs(5) |
| 28 | | ThoracicGr1:STech6:ST:Block=2:Serv 16 Hrs(5) | OrganTransGr1:STech2:ST:Block=2:Serv 13 Hrs(5) |
| 30 | Room: S11 | TraumaMon:STech4:ST:Block=1:Serv 17 Hrs(5) | TraumaTue:STech3:ST:Block=1:Serv 17 Hrs(5) |
| 31 | | TraumaMon:Anes6:AN:Block=1:Serv 17 Hrs(5) | TraumaTue:Anes3:AN:Block=1:Serv 17 Hrs(5) |
| 32 | | TraumaMon:CNurses4:CN:Block=1:Serv 17 Hrs(5) | TraumaTue:CNurse4:CN:Block=1:Serv 17 Hrs(5) |
| 33 | | TraumaMon:STech4:ST:Block=2:Serv 17 Hrs(5) | TraumaTue:STech3:ST:Block=2:Serv 17 Hrs(5) |
| 34 | | TraumaMon:Anes6:AN:Block=2:Serv 17 Hrs(5) | TraumaTue:Anes3:AN:Block=2:Serv 17 Hrs(5) |
| 35 | | TraumaMon:CNurse4:CN:Block=2:Serv 17 Hrs(5) | TraumaTue:CNurse4:CN:Block=2:Serv 17 Hrs(5) |
| 37 | Room: S12 | VasGr1:STech5:ST:Block=1:Serv 12 Hrs(5) | |
| 38 | | VasGr1:Anes4:AN:Block=1:Serv 12 Hrs(5) | |
| 39 | | VasGr1:CNurse3:CN:Block=1:Serv 12 Hrs(5) | |
| 40 | | | Surgeon1:STech4:ST:Block=2:Serv 12 Hrs(5) |
| 41 | | | Surgeon1:Anes5:AN:Block=2:Serv 12 Hrs(5) |
| 42 | | | Surgeon1:CNurse3:CN:Block=2:Serv 12 Hrs(5) |

"Day View" Analytical Map

Process Venue

Macro Objectives

OPTIMIZING STATE TRANSITION SET POINTS FOR SCHEDULE RISK MANAGEMENT

CROSS REFERENCE TO RELATED APPLICATIONS

This patent claims the benefit of priority as a continuation to U.S. patent application Ser. No. 14/473,707, filed on Aug. 29, 2014, entitled "Optimizing State Transition Set Points For Schedule Risk Management," which is herein incorporated by reference in its entirety.

FIELD OF THE INVENTION

The invention relates generally to business scheduling systems, and more particularly to scheduling systems in the clinical setting, such as healthcare delivery institutions or hospitals.

BACKGROUND

The statements in this section merely provide background information related to the disclosure and may not constitute prior art.

Healthcare delivery institutions or environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored can include patient medication orders, medical histories, imaging data, test results, diagnosis information, management information, and/or scheduling information, for example.

Healthcare delivery institutions are business systems that can be designed and operated to achieve their stated missions robustly. As is the case with other business systems such as those designed to provide services and manufactured goods, there are benefits to reducing variation such that the stake-holders within these business systems can focus more fully on the value added core processes that achieve the stated mission and less on activity responding to needless variations such as delays, accelerations, backups, underutilized assets, unplanned overtime by staff and stock outs of material, equipment, people and space that were preventable and/or scheduled for. In this way the system can achieve its mission more reliably and be robust to exogenous forces outside of the process control.

Currently clinical process decisions have historically relied on the art of understanding symptoms and diagnosing causality much in alignment with the practice of the medical diagnosis arts. In an ever-evolving environment, judgment and experientially-developed mental models are utilized by the healthcare providers to utilize the information currently at hand to make decisions. Presented with similar data, the decision made from one maker to another typically exhibits a large variation. Presented with partial information, which is the byproduct of being organized in functional departments, specialties, roles and by the nature of having partial and/or current or dated information availability on hand—clinical process decisions vary widely and typically are locally focused for lack of a systems view upstream and downstream of the decision point.

Where information systems exist, they are simply informational in nature. Examples include scheduled rooms, people, materials and equipment. Recent advances in locating devices such as those utilizing radio-frequency identification (RFID) technology to report a location of a tagged asset are utilized, yet personnel are loath to be tracked by wearing a device. RFID devices are not pervasive, and the systems that monitor them are not fully integrated with the requisite adjacent systems that gather contextual information. The current art is not predictive, probabilistic nor necessarily systemic. For example, knowing the location of an asset is desirable but knowing its anticipated need and interdependencies is required to make a decision to use a located asset actionable. The information required for such a decision comes from a plurality of adjacent health information systems and must have an ability to play forward into the future.

In the current art, current procedure duration and room status is provided without any proactive or forward-looking capability. In the current art, schedules are produced before a day's activities commence. In the current art, process status is displayed along with trending and, often, alarm functionality should a process variable trip a threshold set point.

There is therefore an unmet need for an integrated system and method for scheduling clinical activities and procedures that incorporate variation, staff and equipment preferences, interdependencies and information flow into the clinical delivery of healthcare that can "look ahead" and enable "what-if" capability for prospective decision support.

BRIEF SUMMARY

In view of the above, there is a need for systems, methods, and computer program products which determine schedule risk state and optimize or otherwise improve state transition set points for schedule risk management. The above-mentioned needs are addressed by the subject matter described herein and will be understood in the following specification.

Certain embodiments provide systems and methods for using probabilities to schedule activities in a clinical environment and modify schedules and clinical processes in healthcare delivery.

Certain embodiments provide a computer-implemented method including calculating, using a processor, a cumulative distribution function for one or more tasks in a healthcare protocol for a healthcare facility based on a probability density function associated with task duration for each of the one or more tasks. The example method includes determining, using the processor based on the cumulative distribution function, a plurality of schedule risk states for a task in a healthcare protocol, each schedule risk state associated with an upper specification limit and a lower specification limit along the cumulative distribution function. The example method includes identifying, within the upper specification limit and the lower specification limit for each respective schedule risk state, one or more setpoints associated with one or more probabilities along the cumulative distribution function. The example method includes monitoring, using the processor, execution of the one or more tasks in the healthcare protocol to identify a transition in schedule risk state according to the upper specification limit and lower specification limit. The example method includes triggering, using the processor, an action to react to an actual or upcoming change in schedule risk state based on the one or more setpoints associated with the schedule risk state.

Certain embodiments provide a tangible computer-readable storage medium having a set of instructions for execution on a computer, the set of instructions, when executed, causing the computer to implement a method. The example method includes calculating a cumulative distribution function for one or more tasks in a healthcare protocol for a healthcare facility based on a probability density function associated with task duration for each of the one or more tasks. The example method includes determining, based on the cumulative distribution function, a plurality of schedule risk states for a task in a healthcare protocol, each schedule risk state associated with an upper specification limit and a lower specification limit along the cumulative distribution function. The example method includes identifying, within the upper specification limit and the lower specification limit for each respective schedule risk state, one or more setpoints associated with one or more probabilities along the cumulative distribution function. The example method includes monitoring execution of the one or more tasks in the healthcare protocol to identify a transition in schedule risk state according to the upper specification limit and lower specification limit. The example method includes triggering an action to react to an actual or upcoming change in schedule risk state based on the one or more setpoints associated with the schedule risk state.

Certain examples provide a system including a processor configured to execute instructions to arrange the processor as a logic engine. The example logic engine is arranged to calculate a cumulative distribution function for one or more tasks in a healthcare protocol for a healthcare facility based on a probability density function associated with task duration for each of the one or more tasks. The example logic engine is arranged to determine, based on the cumulative distribution function, a plurality of schedule risk states for a task in a healthcare protocol, each schedule risk state associated with an upper specification limit and a lower specification limit along the cumulative distribution function. The example logic engine is arranged to identify, within the upper specification limit and the lower specification limit for each respective schedule risk state, one or more setpoints associated with one or more probabilities along the cumulative distribution function. The example logic engine is arranged to monitor execution of the one or more tasks in the healthcare protocol to identify a transition in schedule risk state according to the upper specification limit and lower specification limit. The example logic engine is arranged to trigger an action to react to an actual or upcoming change in schedule risk state based on the one or more setpoints associated with the schedule risk state.

DESCRIPTION OF THE DRAWINGS

These and other features, aspects and advantages of the presently described technology will become better understood when the following detailed description is read with reference to the accompanying drawings in which like characters represent like part throughout the drawings. The embodiments shown in the drawings are presented for purposes of illustration only. It should be understood, however, that the present invention is not limited to the arrangements and instrumentality shown in the attached drawings.

FIG. 5 is an exemplary illustration of another user display applicable to embodiments of a user interface.

DETAILED DESCRIPTION

Figure 1:
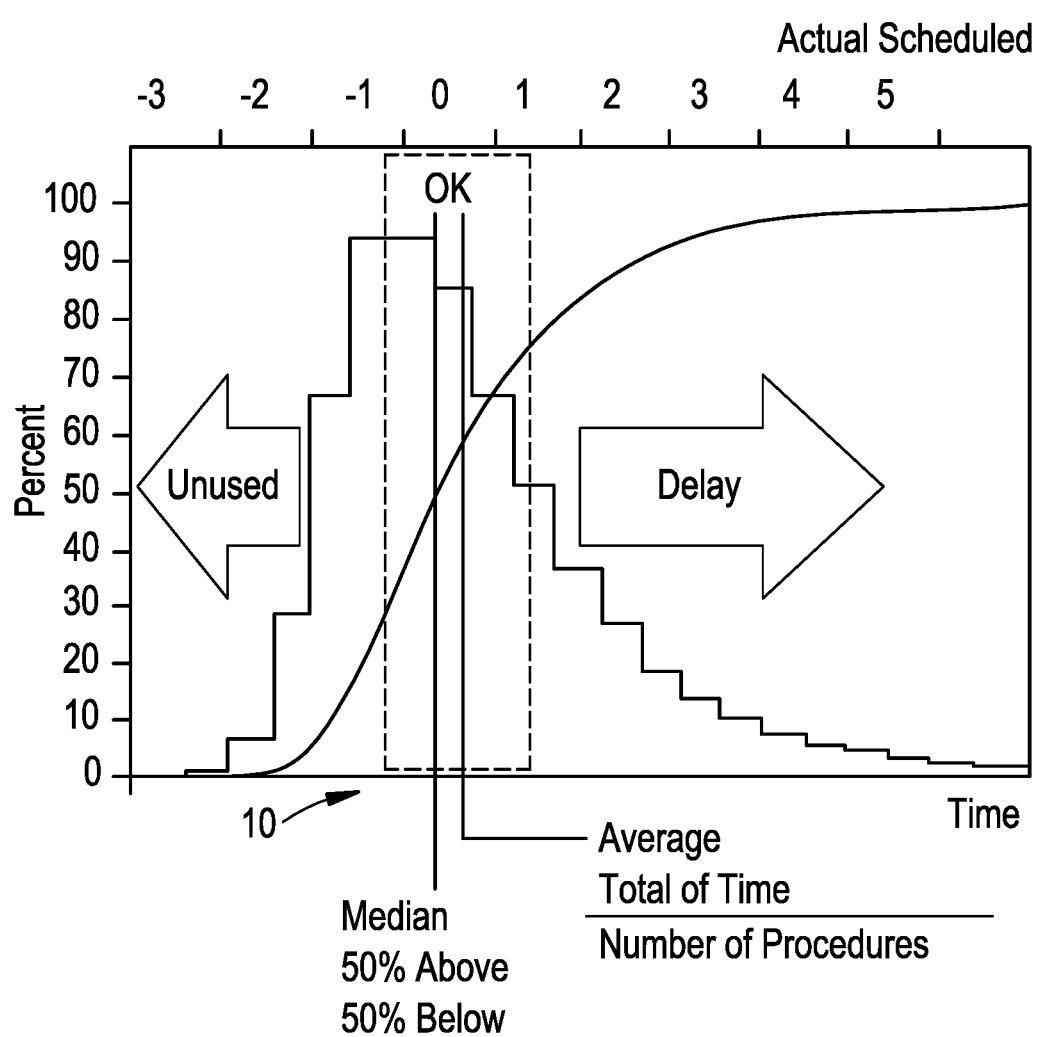
FIG. 1 is an exemplary illustration of the effects of variation on scheduling procedures.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

Certain examples provide systems and methods for systemically organizing tasks and assets of a process to more effectively achieve immediate and longer-term macro objectives. In certain examples, scheduled tasks are organized using, for example, a critical path method (CPM) and the tasks therein are exposed to durations which are probabilistic and are either within the endogenous variation control of the system or are exogenous factors to which the system must be robust to. Measures of duration, availability and reliability to calculate an enumeration of scenarios in the context of variation is used to determine the probabilities of meeting a selected schedule (schedule risk). The probabilistic measures of duration, availability and reliability are functions of path dependent consumption and utilization decisions that are made to determine the use of the assets of the process. Using a multi-modality simulation methodology, for example, a process transfer function of the probabilistic measures may be derived. It is these estimates of duration, both endogenous and exogenous, that are described by simulation that create the task durations and logic for interdependencies which in turn are used to calculate schedule risk in the CPM method. "Schedule risk", as used herein indicates a probability that a task will start at a particular time and end at a particular time. Certain examples manage these probabilities by tracking assets, a state of interdependent resources, and enabling specific operations management workflow down to the person, physical space, an asset or supply that must be made available at a certain time and place. An "optimal" schedule achieves the delivery of care at a specified probability of being completed.

Certain examples provide decision support to help make effective decisions in real time or substantially real time while embedded in a highly variable and interdependent process. These decision support examples can be automated or prescriptive to the process stake-holder.

Certain examples provide a method to review what has recently happened in a process, to view actual current process operations, and to view what is on the schedule looking forward into the near term future. Specific assets such as plant & equipment, people, physical location and information are exemplary entities being tracked.

Certain examples reduce process variation and thereby enable staff to focus more on the clinical delivery of healthcare. This is achieved in at least four ways: (1) An overarching capability to reduce internal (endogenous) variation from interdependency variation that can be anticipated and subsequently managed by techniques such as in certain embodiments of the presently disclosed technology; (2) To incorporate variation into the process planning and control as far forward into the time line such that not only more accurate averages are used for scheduling, but also the probability ranges of time duration for various activities, availability, capability ranges for staff and equipment are incorporated and planned for such as in certain embodiments of the presently disclosed technology; (3) An overarching capability to combine information flows as to the status of staff, patients, equipment and facilities with the scheduled plan such that anticipatory alerts are provided when schedule risk crosses a threshold as well as a diagnosis as to the cause of the likely or actual source of the deviation that is sufficient and actionable enough for intervention by the staff to resolve or revise a plan for it such as is provided for in part by certain embodiments of the presently disclosed technology; and, (4) An overarching capability to understand and incorporate the effects of external (exogenous) variation resulting from unforecastable events such as, for example, surges, medical reason procedure delay, equipment failure and staff sickness such as is provided for in certain embodiments of the presently disclosed technology.

In accordance with first aspect, a system for use in planning procedures is provided comprising the following components: a duration estimator module configured to characterize average duration times and variations from average duration times for a given procedure or activity; a block allocation planner module configured to schedule procedures or activities in accordance with characterized times from the duration estimator module; and a user interface module configured to permit a user to visualize variation, to visualize scheduling opportunities and constraints and to view information output for use in scheduling procedures and activities. Each component or module will be described in greater detail below. In the examples described below, the given schedule is related to a perioperative environment. However it is to be appreciated that the methods and system can be extended to other clinical or non-clinical process systems.

The Duration Estimator, which may be thought of as a 'better ruler to measure with', measures variation so that procedure times are more accurate and so that schedule risk is reduced.

The Block Allocation Planner may be thought of as a "defragmenter" for reserving blocks of time. Much like a computer hard drive defragmenter, it re-sorts the time slots and rooms to be available for the booking of surgeries in such a way as to satisfy constraints and departmental objectives. It factors in preferences and availabilities and solves for the best departmental allocation of space and time and through the allocation, help achieve department policy objectives such as case mix, outcomes, safety and to provide incentive for desired behaviors.

The user interface to the disclosed schedule decision support may include at least one of modules configured to permit a user to visualize variation, to visualize scheduling opportunities and constraints and provide output for use in scheduling procedures and activities, or combinations thereof.

In accordance with certain examples, the scheduling module is configured to aid in initially scheduling activities and procedures and is configured to visualize scheduling opportunities and constraints and will be referred to herein as "Day Planner". Day Planner may be thought of as a manufacturing requisition planner, it enables the scheduling of specific activities and all interdependencies—with the added benefit of simulating forward many alternative plans and contingencies.

In accordance with an exemplary embodiment, the user interface to the schedule manager as the process is occurring is configured to indicate and display variation along with suggestions as to "do-what" and enable "what-if" and will be referred to herein as "Day View". Day View may be thought of as a "radar" for the clinical process, it brings schedule with other location and clinical information so that the staff can know when schedule deviations are occurring, what the cause is, have a way to visualize process interdependencies, have the ability to play out or simulate alternative process decisions and ultimately get the process stakeholders constructively involved in proceeding forward in a manner that has their intellectual buy-in to the course.

A user interface module is configured to provide output for use in directing procedures and activities and will be referred to herein as "Provider/Patient Kiosk". Provider/Patient Kiosk may be thought of as workflow, the kiosk is information gathering and output for the various stakeholders in the clinical process. It gathers information that is later used to reduce variation and it interacts with the stakeholders in mediums that are natural extensions of their native environments. The user interface may include computer display and/or reports.

It is to be appreciated that the clinical process decision support methods may include one or more of the capabilities described above, as well as any combination thereof.

Endogenous variation is reduced within clinical process from situations arising from concurrent scheduled use of mutually exclusive resources such as doctors, nurses, equipment and space regardless of the cause being endogenously or exogenously perturbed. Methods according to the present invention move clinical process decisioning as far forward into the care process as possible. Known interdependencies are then brought to each decision point and factored in so that interdependencies are then managed and visible immediately. For example, in the instance of day planning/scheduling done in advance of the day for which activity is scheduled, some interdependencies must be known well before block schedules are derived and patients are scheduled.

Certain examples address the immediate, inevitable deviations from plan with diagnoses capability, in near real time, for the causality of endogenously generated variation and provides decision support for prospective process recovery to either the originally proscribed state or a new, superior one, given other operating constraints that render the original plan less advantageous. Exogenous variation—that which happens to the delivery system, despite the care and safety margin in the process scheduling, such as for example unanticipated medical complications, a surge of additional procedure(s) or an unanticipatable staffing change or equipment outage—is addressed by the ability to see the impact of change at or before it is currently possible to see it and then to provide feasible path forward decision support.

A key enabler of designing out preventable variation and to making allowances for residual normal variation is the time constant to detect change and make decisions. The decisioning time constant is enabled via the disclosed methods and systems to fall within the time constant of unrecoverable process oscillation.

Major sources of endogenous variation resulting from interdependencies amongst resources are, for an exemplary embodiment in the perioperative environment, delayed assets of the process due to unanticipated complexities of interdependent activities, equipment breakdown, incomplete preparation, staff sickness, patients not biometrically responding to procedures, operating complexities and the like.

Certain examples include Duration Estimator, Block Allocation Planner, Day View, Day Planner/Day Replay and Provider/Patient Kiosk as elements for information and decisioning designed to reduce systemic variations by eliminating schedule risk up front and enabling rapid on-the-fly response to unanticipated perturbations to the clinical process, for example.

It is advantageous to not only know what is scheduled, but to know that what is scheduled is robust to unplanned events, to have an assessment of the schedule risk, to have the ability to visualize likely process scenarios before hand, to be able to determine robust decisions that can be taken in the dynamic environment that will best achieve the operating objectives, to learn from what transpired, to achieve departmental objectives and to include stakeholders in the clinical process. Each of these advantageous capabilities is advanced with certain embodiments of the present invention.

While prior approaches involve point estimates to account for delays, certain examples instead analyze the underlying physics of complex, interdependent processes with coupling amongst shared resources and durations that are anything but point estimates. Certain examples overcome effects of variation by consuming probabilistic forecasts, calculating true delays, and recasting a "feasible" schedule from an absolute to a comparative level of operating risk. Certain examples diagnose sources of delays by computing specific causal relationships as opposed to hoping that a prior art scheduling system showing availability means all interdependencies are resolved (they never are). Certain examples provide a specific, actionable workflow tied to specific staff, equipment, space, supplies and patients. Certain examples allow a forecast or view into the future based upon a current state of chaos and identify specific tasks that will otherwise be delayed in the future. Certain examples can estimate a degree of schedule robustness by superimposing, onto a schedule, external probabilistic demand changes of adds and drops as well as internal capability readiness such as machine or inventory availability.

By analyzing stochastic processes and approaching a schedule with degrees of feasibility rather than absolute feasibility, schedule modification can be facilitated to maintain robust schedules in which targeted and specific workflows should be triggered ahead of bottlenecks building delays. Certain examples approach medical services as a series of component tasks rather an "all or nothing" proposition. Instead, a medical service can start if it is known when, after a start, the next critical path resource will be available. Another key insight is the human factor: care providers do not accept a black box schedule once operations degrade; they want to "what-if" and see how the system responds not only in the present but through the day, so that a sense of schedule risk can be understood. Further, modern care delivery must be more productive than 5 years ago, than a decade ago; schedule "slop" is trimmed by necessity. As that safety margin is removed, other prior scheduling methods will fail.

Referring to FIG. 1, a representative illustration of how variation impacts scheduling is shown. Typically the average time for a given procedure is subject to variation due to a variety of reasons. However, a healthcare institution or hospital schedules procedures based on average time duration per procedure. Therefore, if a number of procedures take longer than expected then the remainder of scheduled procedures may be delayed or rescheduled. Conversely, if procedures take less time than expected then there is a risk of unused availability. Both underutilization and scheduling delays are costly in time and resources.

Clinical procedures have vast variation yet the advanced scheduling typically is made at a single prescribed duration time. When procedures take less than the forecast (typically estimated in the prior art as the average for a procedure plus, perhaps, a safety margin), valuable assets are underutilized and clinical flexibility is degraded because the availability is unanticipated/unactionable and further, downstream processes are impacted from patient handling, staffing and equipment turn around. When procedures take more time than forecasted, valuable assets are unavailable for other procedures that were scheduled thus backing up upstream processes, creating staffing shortfalls and fatigue stress from the emotional responses to schedule collapse and recovery.

Estimating the duration of a procedure has a number of difficulties. One forecast difficulty is the variation on single procedure cases that result from doctor/staff combinations, patient disease state severity, patient medical complications and physical attributes such as weight/height/body mass index (BMI)/surface area, information availability, equipment and supply availability, day of week, procedure prior and etc. Another still is wrong or non-recorded information such as, for example, time durations, and multiple procedures conducted with only a subset being recorded as actually having been conducted.

The objective of understanding the variance in procedure duration is so that the schedules may be made more robust. How schedules are made robust will be discussed below with reference to a module referred to as Day Planner. It can be understood what the interactions of factors are on specific procedure combinations or alternatively, to classify combinations of factors into defined duration probability densities. Either the procedure is called in a schedule planning simulation or using the time density functions directly, for example.

Figure 2:
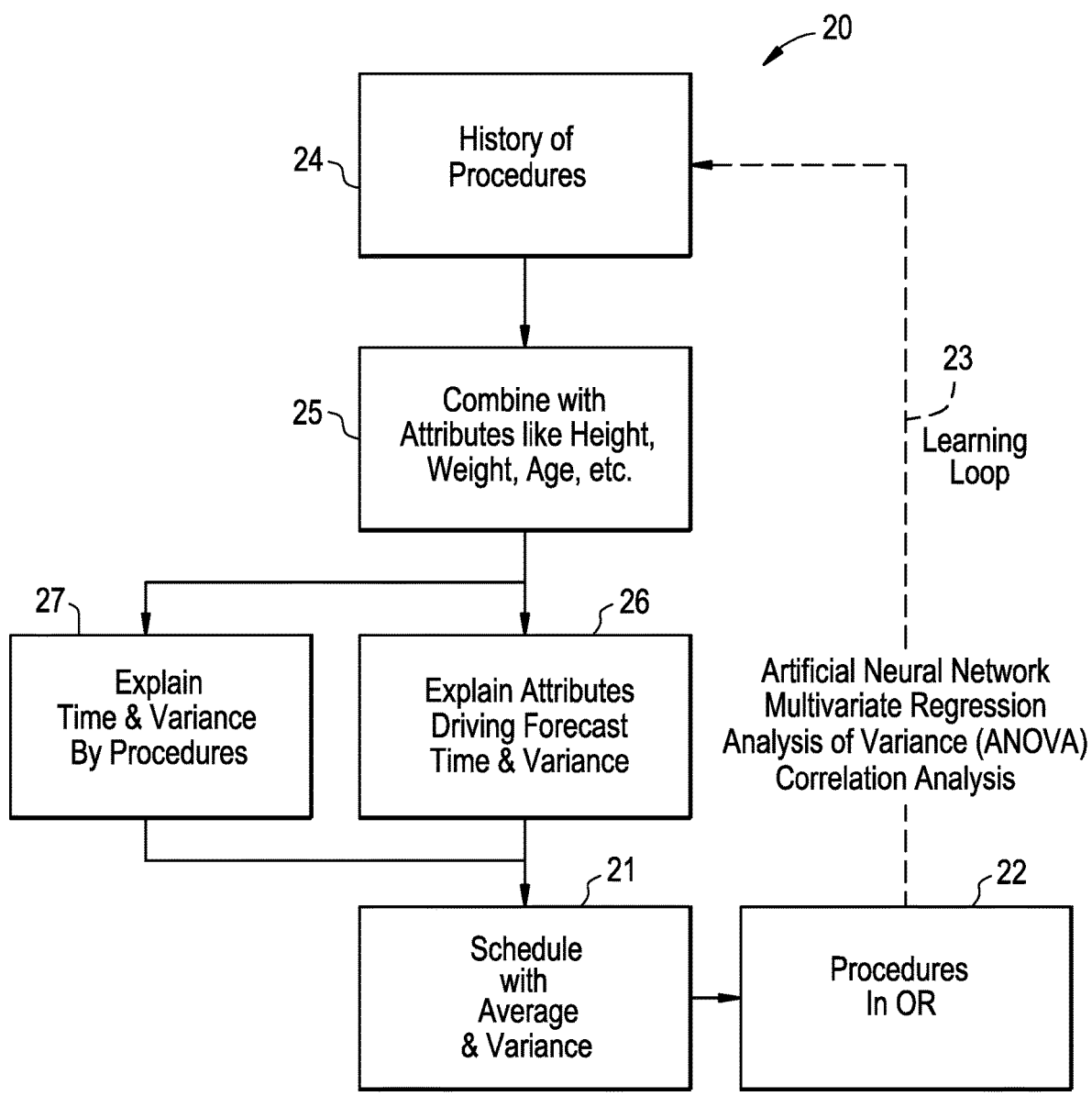
FIG. 2 is a block diagram illustration of an embodiment of a duration estimator module to which embodiments disclosed and described herein are applicable.

Referring to FIG. 2, an example Duration Estimator module is shown. Duration estimation is accomplished depending upon the information initially available, for example a history of procedures 24, and then a learning loop 23 is implemented that reduces the forecast error by incorporating additional information such as accurate case times and well measured descriptive attributes that serve as leading indicators. In an embodiment of duration estimation as shown in FIG. 2, a procedure is scheduled with average known time and variance at step 21 for a procedure, e.g. in the operating room (OR) at step 22. Additionally, the history 24, like attributes 25, and variation explained at steps 26 and 27 are then incorporated into forecasting and scheduling.

In the absence of a historical record, duration estimation is achieved via expert input (not shown separately but can be included in history 24). Experts include consensus of relevant professionals collated via industry working groups, societies and academic study, nursing, administrators, anesthesiologists and surgeons. Historical data of recorded procedures and their duration are more desirous than strictly expert opinion. A preliminary analytical step is to characterize the accuracy (mean and statistical variation) of historical procedure duration vs. actual for like cases. This is achieved with a design of experiments on a subset of procedure and/or procedure clustering and then compared to the historical record. Additionally, audits are conducted to compare scheduled vs. recorded as being conducted. Art from the methods of gauge repeatability and reliability are then used to characterize the confidence interval of forecasted duration. Regardless of the accuracy, a measure of duration classification is made and its degree of uncertainty is established.

FIG. 1 depicts a concept reflected in Duration Estimation. Earlier than anticipated finishes may afford additional schedule margin if only visibility existed either at the time of booking or once the procedure(s) began that a room would have capacity. Likewise, delays ascertainable at scheduling or during the procedure, if better understood, would impact the interdependencies downstream of the procedure both for that clustering of patient/staff/asset and for other impacted clusters. The schedule robustness is attained from planning the median, average and a notion of anticipated variation such as standard deviation. Within this window 10, indicated as a dotted line, and adjustable and/or tunable via stochastic optimization, the system level schedule is made to be robust (having a selectable and tunable probability expectation).

The history of procedures is combined into a relational database or spreadsheet or analytical platform capable of data mining with data incorporated into a data repository. The objective is to regress potential leading indicators against the historical duration times in an attempt to incorporate significant predictive variables that can then be used at the time of booking to allocate time.

Where it is possible to describe variation with enough confidence, then the regression equation is utilized plus a fraction of the variation to set the duration. In calculating what is 'enough confidence', a fraction of the variation is included in addition to the calculated duration using the regression equation.

Enough confidence is a function of the case throughput for a period, typically defined as a day given that there is a slack time off hours for schedule catch-ups to be made day to day. The cumulative probability density function for all cases in an allocated day is set to a level of schedule risk at a given time within the day. This would be expressed as a desire to be, for example, that the caseload can be processed by 7 PM with 90% confidence. A back propagation to the discrete cases is made such that the individual error terms (variation) are incorporated to the calculated duration in fractional steps until such time as the portfolio of cases can meet the daily throughput/risk setpoints. This may be performed manually or with the assistance of a stochastic optimization.

It can be the case that historical data is insufficient to separate between procedure(s) with statistical significance given the available leading indicators. In this instance, the histogram of all procedures can be partitioned and procedures that cannot be statistically separated may be clustered such that each is associated with a probability density function (PDF) of time duration. The total of the PDFs form the complete enumeration of the historical procedures less holdouts of known data defects A learning loop 23 is established that finely records attributes and procedure times. As is the case when first classifying duration from the historical record, techniques including Artificial Neural Networks, Multivariate Regression, Analysis of Variance (ANOVA) and Correlation Analysis are used to refine predictive capability and tighten the confidence bounds. Additionally new descriptive attributes may be appended in order to test and improve forecast accuracy.

Figure 3:
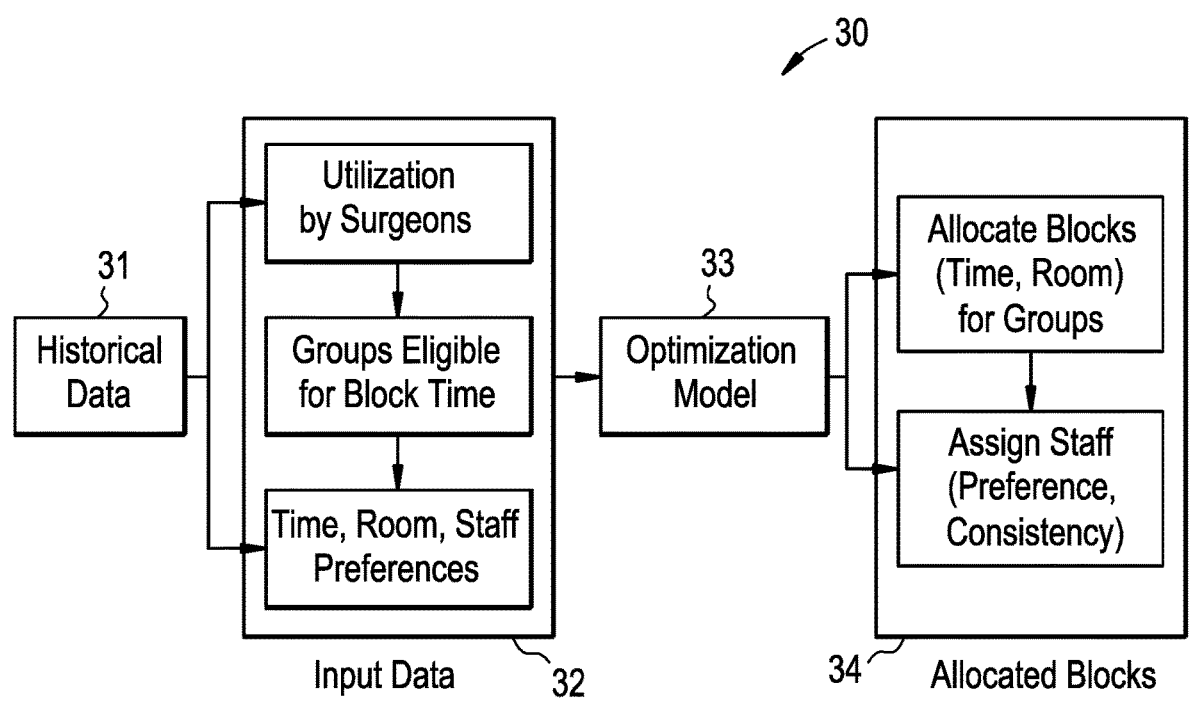
FIG. 3 is a block diagram illustration of an embodiment of a block allocation planner module to which embodiments disclosed and described herein are applicable.

Referring now to FIG. 3, an embodiment for a Block Allocation Planner module 30 is shown. Healthcare stakeholders need a cadence to which schedules for room, staff, equipment and patients can be scheduled into in such a way that achieves the provider's mission and operating objectives. Procedures are booked into the available blocks. This process is well described in the literature with a number of commercial applications serving this function.

What does not exist is a method and system to allocate block time in such a way as to simultaneously satisfy stakeholder preferences. Additionally, there is a present need to have available in the market an engine to 're-sort' block allocation from time to time in an institution. Similar to the need for a defragmenter utility for a computer hard drive—healthcare blocks are allocated based upon past, evolutionary activity. Staff, rooms, procedures, patient demographics, clinical specialties and competitors all drive changing assumptions of former time and space allocations.

It is to be appreciated that methods and systems described herein may enable increased throughput, schedule risk reduction, incentive driven policy, preferences and a consistent environment. Hospitals, surgeons, patients and staff are beneficiaries.

The method proceeds as depicted in FIG. 3 showing the Block Allocation module. At step 32, input data such as utilization by surgeons, groups eligible for block time and time, room and staff preferences are provided. As used herein, the term "block" refers to an allotted time frame such as for scheduling an operating room or clinical procedure room, e.g. imaging room. Historical block allocation data is characterized by the art of data mining to describe utilization by surgeon. Hospital administration determines the groups eligible for block time and preliminarily reconciles requests. The preferences are identified both by historical check and by communication to the stakeholders—between surgeons and nurses, surgeons and rooms, equipment and precedent/antecedent procedures, anesthesiologists and other logistical requests. Administration sets objectives such as the degree of concurrent satisfaction of the preferences, departmental goals such as throughput, case mix, doctor mix and departmental outcomes. A multi-criteria optimization is run at step 33. At step 34, staff is subsequently assigned to operating rooms.

Figure 4:
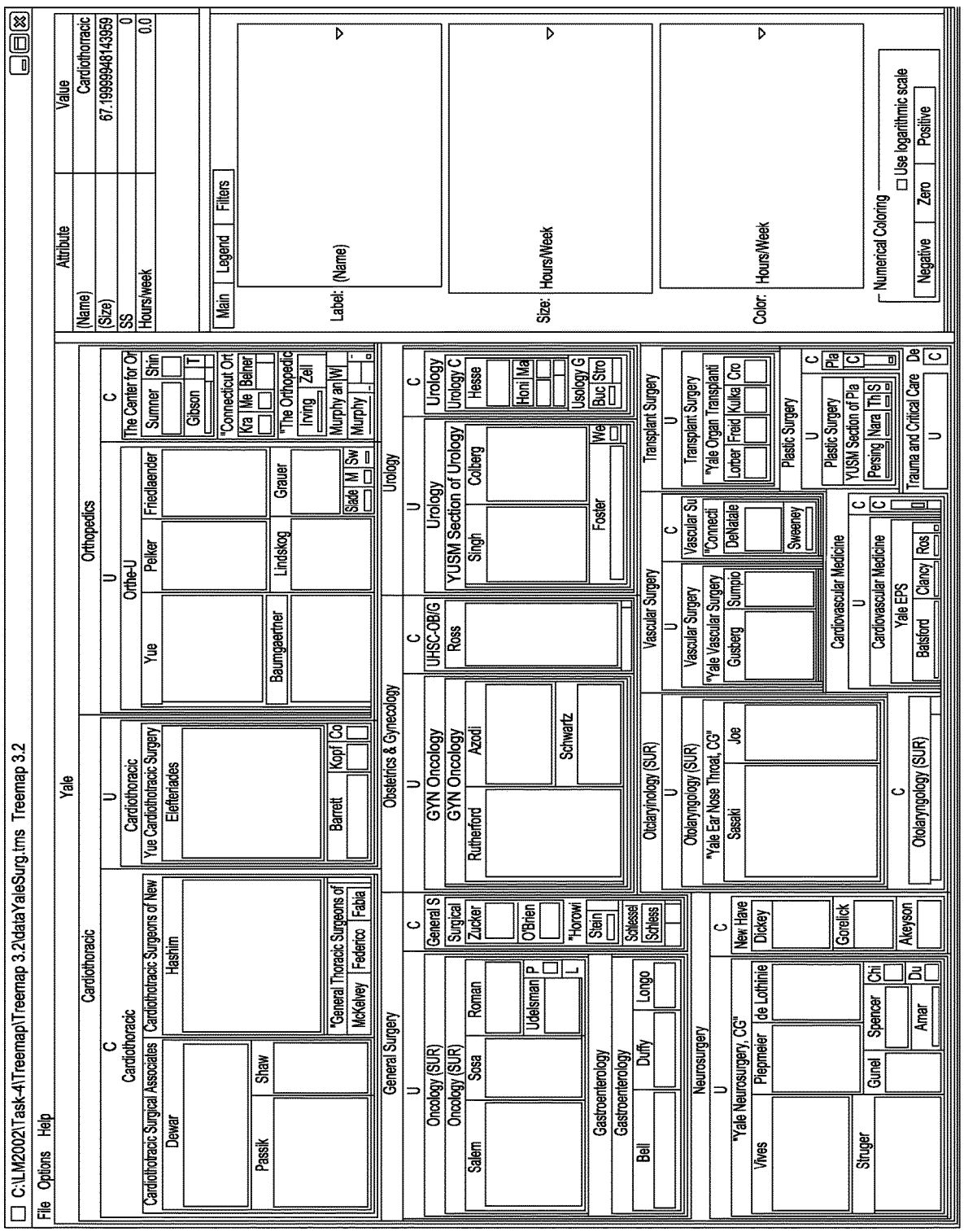
FIG. 4 is an illustration of a user display for an exemplary block allocation planner module.

Objective decision-making is an explicit benefit of the disclosed system. Having the ability to communicate visually is key to rapid understanding. A 'cockpit' describing the historical fact patterns and current operating results is key to facilitating conversation. The use of cockpits has been described in other known business systems. A further extension is depicted in FIG. 4.

The block schedule output may take many forms. An example block schedule output is shown in FIG. 5.

In certain examples, a user interface module may be provided in order to get information to a user for use in scheduling procedures. In an exemplary embodiment, user interface comprise the ability to monitor activities for a given day, and will be referred herein as "Day View". Day View may be thought of as being a radar for the perioperative environment coupled to a logic engine. More that simply alarming a problem, Day View prospectively assesses interdependencies such as, for example, a certain procedure and a piece of equipment and staff required for the procedure. Should the location and availability not be per the schedule, an alarm is first made as a warning for action. If as the time of need approaches, the interdependent items are located via passive and active identification. If the issue can be resolved such as via a phone call or quick action—an issue was avoided or minimized.

Should the interdependency not be solved, Day View has the capability to simultaneously solve for all other interdependencies and allow a 'what-if' scenario testing exercise to occur. The what-if may be manual or automatic.

By having a procedure finish before the schedule, potential scheduling flexibility is lost for other issues that inevitably arise during the day such as staff availability, rooms and equipment constraints. Potential throughput capacity might also be impacted in that over the course of a day, one or more additional procedures could be inserted into the schedule.

A longer than anticipated procedure can have the effect of backing up other dependent procedures for a particular patient either in the original department or cross departmentally. Additionally, the rooms and assets that were originally allocated are no longer as available and therefore other patients and activities are negatively impacted. There may be unscheduled overtime of staff or extra costs associated with turning around apparatus. New schedules must be made that impacts reworking of staff planning as well as the potential for rework on case preparation for following or interdependent procedures. The anticipated and/or needed throughput capacity may also be impacted negatively. These changes reduce operating flexibility and increase the anxiety of the clinical process stakeholders—often leading to what is commonly known as 'burn-out' and attrition, as well as to the potential ultimate quality of delivered healthcare.

Figure 6:
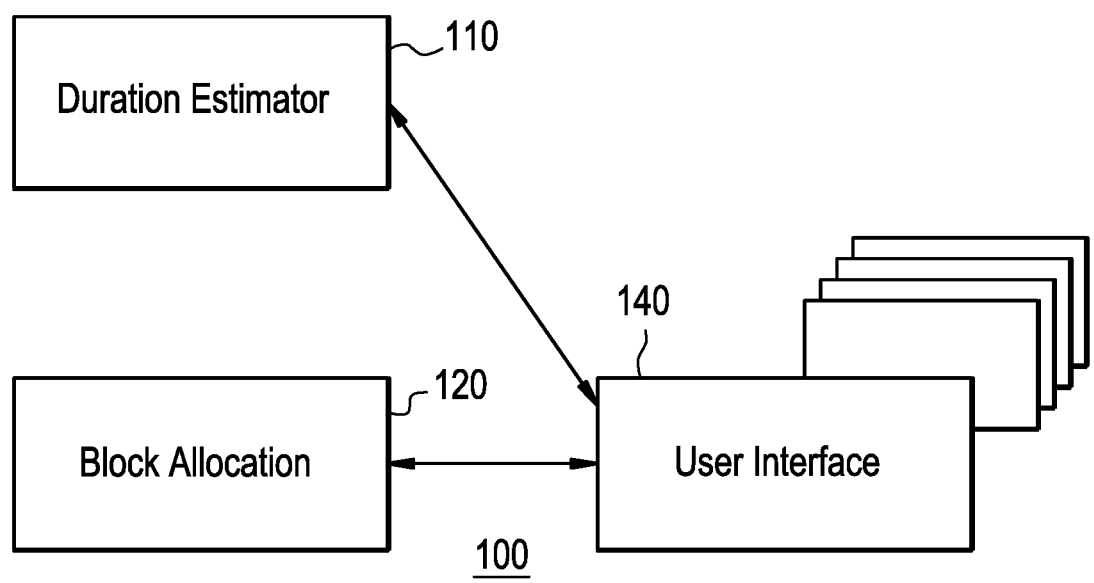
FIG. 6 is a block diagram illustration of a system for use in planning clinical procedures in accordance with embodiments disclosed and described herein.

Referring now to FIG. 6, a block diagram illustration of a system for use in planning clinical procedures in accordance with certain examples. System 100 includes a duration estimator module 110, block allocation planner module 120 and user interface 130 as described in detail above. While examples have been described with reference to a clinical setting, it is to be appreciated that other environments may also benefit from similar methods and modules described herein.

Certain examples provide a proactive application looking ahead at procedure scheduling and duration to avoid delays by triggering an advanced warning with sufficient time to respond in an event that scheduled procedures will start or end before or after their scheduled time. Certain examples provide recommendation regarding one or more specific decision(s) or action(s) can be taken to add, drop or move specific cases, task and assets, for example.

In certain examples, scheduling is provided that accounts for available personnel, available physical space, and available blocks of time, for example. Certain examples account for variations associated with fluctuating demand and asset availability.

In certain examples, multiple criteria may be set for a scheduling process. Additionally, various risks associated with selected criteria may be taken into account. Furthermore, rather than providing a single schedule that is designed with average or generic or judgmental time buffers to compensate for variation, certain examples enable a plurality of scheduling scenarios to be manually or dynamically entered or simulated automatically to explore an available solution space and ramifications on current and future activities. Certain examples provide suggested decisions calculated to help meet one or more static, dynamic or path-dependent configurable objectives.

In certain examples, a scheduler provides a capability to view a single or multiple process metric, agent, and/or asset of the process as well as a dynamic impact on interdependencies such that one or more causes of variation in that process may be explicitly communicated and understood. Certain examples enable a dynamic view to process risk along one or more dimensions in real time (or substantially real time with some inherent system delay) or historically, for example. Additionally, certain examples may prompt an alarm, action and/or warning if a certain process variable trips a threshold set point, for example.

In certain examples, multiple simulation modalities are employed including a critical path method coupled to discrete event, agent, Monte Carlo and/or continuous simulation. Using this coupling, one or more objectives of the process may be assessed.

In certain examples, Day View or other user scheduler interface provides features for historical review such as replaying a day or past several days in order to extract from and discover process dynamics, training, and knowledge capture for future use as well as for administrative activity cost(s), protocol verification and billing, for example.

Utilization and asset consumption may be viewed to help understand a state of dynamic interdependencies between scheduling processes and to help determine which a schedule is likely to be met. If a determination is made that a schedule is not likely to be met, data may be viewed and/or used to help identify what assets and interdependencies are causes of schedule variance.

A future schedule view may be provided to calculate "what-if" scenario testing to help understand schedule changes and effects of endogenous variation, such as schedule adds or drops, resource availability, unforeseen delays or failures, etc. Future schedule extrapolation helps to enable a higher process entitlement via better decisions that directly and indirectly affect variation and throughput, wait times, stocks, capability and uses of assets in procedure and resource scheduling.

Thus certain examples provide scheduling of processes in highly dynamic environments where knowledge workers and service providers are integral agents of the process, rather than providing singular or discrete schedules with an objective and buffers allocated by judgment or heuristics alone.

While many processes benefit from embodiments disclosed herein, an example involving a hospital perioperative clinical healthcare delivery process is used for purposes of illustration only.

In an example clinical process, a schedule may be derived among available assets with well-understood interdependencies. For example, a doctor cannot be in two locations at once, and a surgery may not progress unless, concurrently, the appropriate patient, doctors, nurses, information and equipment are in an operating environment suited for the procedure. Additionally, the biometrical state of the patient should be adequate for a surgery to proceed.

Figure 7:
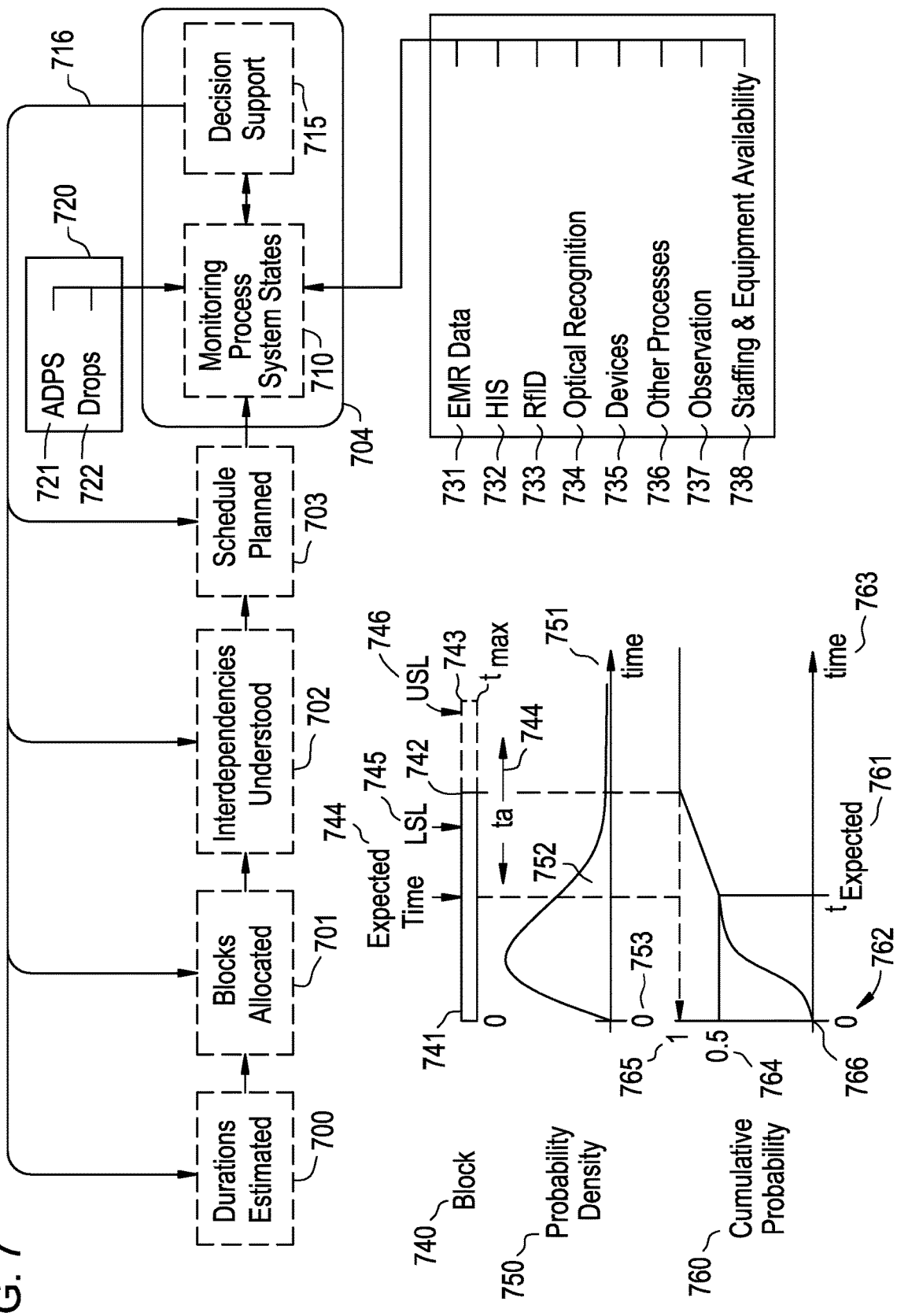
FIG. 7 illustrates the Day View system in its process context according to embodiments disclosed and described herein.

FIG. 7 illustrates the Day View system in its process context according to an example. FIG. 7 illustrates task(s) results in creation of the day's first generation of a schedule, for example. This schedule is then dynamically modified as endogenous and exogenous factors change. The schedules as delivered at the start of the day and as they change during the day have risk. Risk being defined here as the chances of not making the schedule. Day View provides systems and methods for estimating this risk and establishing corresponding alarm set points to minimize risks.

As shown in the flow of FIG. 7, Day View may estimate durations from a historical book or record of business. If no historical data exists, data from other related facilities may be used, for example. In certain embodiments, users may subscribe to services to receive or exchange data to aid in duration estimation and other calculation, for example. Additionally, access to other user data may allow comparison of procedure times between users/institutions, for example. After duration estimation, block allocation occurs. Then, interdependencies (e.g., one x-ray machine needed in two rooms; people, surgeons, instruments, etc., needed in multiple places/times; etc.) are planned into the schedule. Then, Day View monitors activity as the day progresses in order to add, drop and/or otherwise intervene in a schedule with automated adjustment and/or decision support. Other input, such as electronic medical record (EMR) systems, healthcare information systems (HIS), status/monitoring systems (e.g., radio frequency identification, RFID, patient call systems, patient bed monitoring, clinical systems and etc), optical recognition for shape of instrument/operating room activity, devices (e.g., electrocardiogram (EKG), anesthesiology, etc.), interaction with other processes, manual observations, staffing/equipment availability, may feed into Day View for correlation with a schedule or protocol.

In certain embodiments, a determination of an initial view of a schedule may be prefaced by a sequence of analytical work. Referring to FIG. 7, activity durations 700 are utilized to schedule time within available limits. In the example embodiment, blocks of time 701 are defined within which procedures may be booked for or by those entitled to provide perioperative service.

Responsible scheduling is considered to include an estimate of duration and a block of time allocation within which the procedure is considered likely to finish. While under-scheduling procedure time creates delays in subsequent procedure starts, over-estimating and blocking time for available assets may create under-utilized capacity.

When average duration forecasts are used in a clinical environment, and each room is considered unique outside the context of the staff's before and after tasks, chaos often results from concurrent demands. Utilizing probability density functions 750 of time for a given duration estimation of a surgery is a foundation for calculating a schedule's risk and system level performance or optimization, for example.

Referring to FIG. 7, a probability density function (PDF) of time 752 for a procedure is calculated, typically from historical records of similar procedures. The historical frequencies, in histogram form, for example, are normalized by one or more standard statistical techniques to create the PDF with area=1. Certain embodiments record information including actual procedure code(s), time(s), staff patient specifics and process environment 730, for example.

A schedule risk is calculated by integrating the PDF using well understood statistical techniques to create a cumulative probability density function (CPDF, also referred to as a cumulative distribution function (CDF)) for duration CPDF 760 where a probability of duration is made available. Given sufficient time 763, there is a 100% chance of the forecast duration matching the actual procedure duration. Likewise, given no time 762 there would be no probability of completing the surgery within the time interval. The expected time to complete similar tasks are found at the 50% probability 764 and is $T_{expected}$ 761, which is the time where it is 50% likely the procedure will finish sooner and 50% likely that it will take longer than this time value. The scale of time zero 762 and maximum 763 is continuous and directly related to probability zero 766 to 100% 765 according to the PDF cumulative probability density function transform.

A risk that a procedure will not finish within its allotted time is determined by a probability 760 at the time allocation scheduled for the procedure. Again referring to FIG. 7, the block of time reserved 740 is conceptually superimposed upon the PDF and CPDF aligned at time equal zero 741, 753, 762 with the same time scale such that the maximum time 743, 751, 763 are aligned. For any selected block of time allocated 742, the probability of the actual procedure completing at or before that time is found from the CPDF 760. The allocated time 744 is a decision variable available to the scheduler and/or optimization algorithm used to achieve the schedule's objectives.

A lower specification limit, LSL 745, and upper specification limit, USL 746, are similarly available. The LSL 745 is a minimum probability threshold (the most schedule risk) of completing the procedure within the allocated time. The USL 746 is a degree of what is typically referred to as "cushion" or "margin" in that it is the adjustable surplus probability over an expected duration probability 764. The LSL 745 and USL 746 are adjustable parameters and may be used as logical rules in decision support 715 available to manual or automated scheduling. The set points may be tuned in a learning feedback loop that uses observed historical process data 862, learns probability set points 742, 745, 746, 761 to optimize throughput and cost and offers optimized time allocation and probabilistic set point decision support.

Certain examples facilitate dynamic, intelligent schedule change based on changes in the actual stochastic and interdependent processes of care occurring in the hospital. This method involves forecast durations of procedures arranged within a schedule along with interdependencies of space, people, equipment, consumables and information (e.g., 700, 701, 702, 703). Actual process feedback is provided such as from HIS, RFID, Optical recognition, telemetry and various clinical systems. An explicit mapping of interdependencies in process assets, such as those exemplified in FIG. 10 and their related task probabilistic durations of activities is coupled to the system's simulation capability for finding feasible solutions.

Examples of events necessitating modification to the schedule 703 include staff and equipment unavailability 738, upstream or downstream processes not able to provide or receive patients 736, devices needed in the scheduled tasks not functioning 735, people and equipment not in planned location 733, 734, inputs from clinical or administrative systems not adequate 732, patient biomedical adequacy or health status not within specification 731, added procedures 721 not in the schedule 703, and dropped procedures 722 for any reason. The schedule may be modified by changing assumptions 716 in the activities 700, 701, 702, 703 used to create the schedule or dynamically managed in the Day View system 704. The changes to assumptions 716 may be manual or computer generated to exploit feasible solutions.

In an environment involving many interdependencies, variation in any interdependent factor may propagate process disturbance. Certain examples help facilitate understanding and proactive management of factors that, if delayed or accelerated from plan, will likely increase the probability of delay and preclude a process operating objective from being met.

Returning to FIG. 7, scheduling process interdependencies are analyzed at 702. As an illustrative example, a patient's vital biometrical readings should be within surgical protocol specifications prior to the administration of anesthesia. Surgery (and Surgeon) commencement is dependent upon anesthesiology, which, among other factors, is dependent upon the patient's biological readiness for the forthcoming procedure(s). Certain examples provide management of interdependencies in such a way that the appropriate factors are given action if those factors, left unmanaged or along current trajectory, would delay the schedule or diminish the process objectives. For example, in the illustration, it may be that the surgeon is required to be scrubbed in at the time of anesthesiology. However, given the patient's biometrical state, the surgeon is not actually an impediment to starting surgery. Thus, factors affecting biometrics are illuminated as important tasks, and interdependent people, equipment, space, and information are given an estimated time before returning to critical path.

Figure 8:
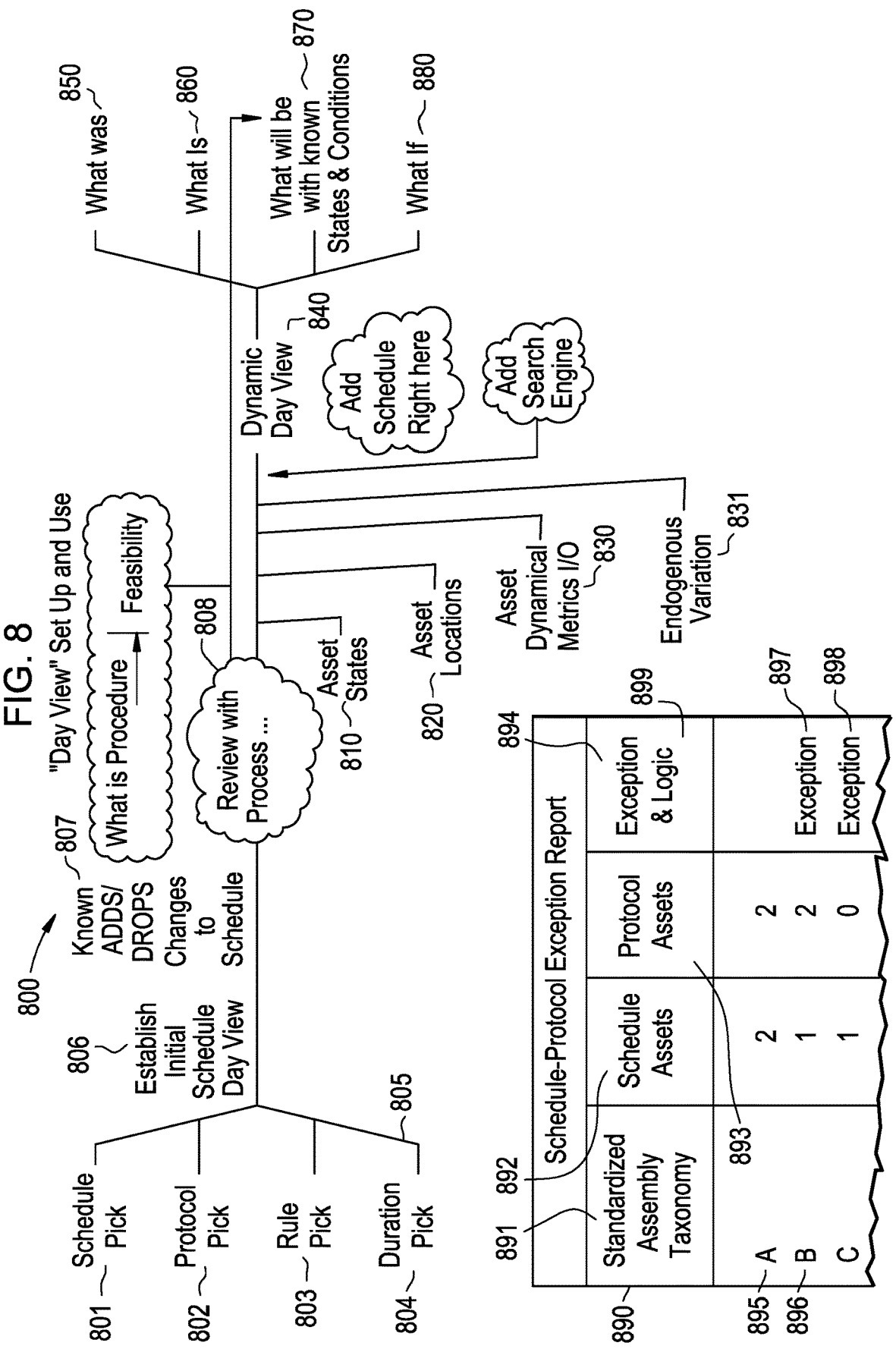
FIG. 8 illustrates an exemplary setup and use of the Day View system in accordance with embodiments disclosed and described herein.

FIG. 8 illustrates an example setup and use of the Day View system in accordance with certain examples. Building blocks of information which allow calculation of schedule risk, an ability to proactively manage root cause variation and produce historical "what was" emulation, "what is" visualization, "what will be" simulation, and "what if" simulated scenario generation are provided. In certain examples, the method may be used to compare protocol requirements to the actual or generated schedule.

In accordance with FIG. 8, the Day View system is set up for the day by selecting protocol(s) that are supposed to happen, loading a schedule to execute the protocols based upon a patient's care plan, selecting decision rules to resolve interdependencies, and selecting probable durations, for example. Previously-unscheduled surgical cases that need to happen that day are added and dropped procedures are removed. Once the day commences, a state of assets, personnel, equipment, rooms, etc., are monitored to determine their status. Dynamic metrics and variation in clinical processes are determined during the day. As the day progresses, schedule risk is reiteratively calculated, and a determination is made to adjust the schedule. Using Day View, a system and/or user can see what has happened, what is happening, what will likely happen given what we know, and can simulate what-if scenarios. The system and/or user can then minimize underutilized capacity, reduce delay or improve patient, doctor, nurse allocation by adjusting scheduling.

The dynamic Day View 800 is constructed via the execution of analytical tasks as depicted in FIG. 8 in accordance with certain examples. The disclosed analytical tasks 800 may be performed manually. However, the Day View system enables these tasks 800 with an electronic workflow that extracts, transforms and loads data and then executes algorithms in sequence. Relevant algorithms may be executed using a method and system disclosed by Akbay and Alkemper known as Decision Execution System, via hard-coded computer logic, and/or via configuration of commercial Extract-Transform-Load and workflow tools, for example.

As illustrated in FIG. 8, an initial schedule view 806 is established with, for example, four building blocks 801, 802, 803, and 804. An initial schedule 801, 703 is obtained to provide a scheduled time, place, activity, based upon the care plan protocols required and the related assets (e.g., FIG. 10) of the process. Second, a clinical protocol 802 of the procedure is identified. A protocol establishes what assets and procedures make up a process, for example.

General agreement should exist between the schedule 801 and protocol 802. Referring to FIG. 8, schedule—protocol exceptions are identified by comparing a count of requisite assets in a structured way 890. A taxonomy of standardized asset names 891 is populated with the count of scheduled assets 703, 801, 892 and those called for by protocol 802 for each category called for by the taxonomy 891. Where the number of assets matches, there is no exception. This is illustrated by line item 895, for example. Where the number of specific assets called for by protocol 893 exceeds those that are scheduled 892, an exception 897 is made apparent. Certain examples provide configurability as to how the exception is reported: scheduled to protocol or visa versa 899, for example. Alternatively, there may be more assets scheduled than requested by protocol 898, and that is illuminated.

A third of four uploads of data to establish the initial schedule Day View includes a Decision Support rule set 803. The rule set 803 encapsulates the logic specific to protocol and process. An illustrative example relates to a specialized surgical tool. A sterilized probe should be available in a surgical case cart. If a probe is not available, the surgery may proceed if there are two probes on standby on the preoperative floor. Logic 803, 715 may be rule-based, example-based, evidential reasoning, fuzzy logic-based, case-based, and/or other artificial intelligence-based logic, for example.

A fourth upload of data is the duration estimation PDF portfolio. Alternatively, rather than replicate an instance of this knowledge base 804, the analytical workflow 805 may have access to the Duration Classification Engine 700 deployed in the scheduling operation.

Known additions and deletions 807 are made to the initial schedule 806. Illustrative examples include a request to add an emergency surgery to a day, a staff person calls in sick, etc. Timing of this activity 807 has maximum utility if done before the start of scheduled activities and sufficiently in advance to allow time for staff review of the upcoming tasks 808.

A review of an upcoming period's process task, schedule risks and contingency plans is beneficial to provide a contextual understanding of activities as well as to solicit opinions of staff to then modify the schedule for improvement. It may also be beneficial for individual and team preparation and training, for example. At any point, schedule tasks and assets may be simulated forward. Utility may be gained in shift change handovers, for example.

At the start of scheduled activities, variations may begin to occur. Certain examples help to manage variation systemically in such a way as to meet the objective of a schedule without needless non-value-added activity, such as efforts to complete actions at a rate impacting a critical path for a schedule.

Day View manages a scheduling critical path by monitoring factors that will impact the critical path. If scheduling assets are in designated location(s) and state(s) of availability, a schedule can execute as planned. If a state of an asset in a process or an activity of the process is delayed or accelerated from its designated time, place and state, a chain of dependencies may be impacted. Day View instantaneously calculates durations and the scheduled risks 706 and alarms at probabilistic set points 811, 813, 815.

Asset states 810 are relevant degrees to which an asset is available or biometrical states of a patient. As an illustrative example, a certain piece of equipment is an asset in a schedule process, and a desired state of that asset at a beginning of a designated surgical procedure is to be calibrated and sterile. The state of the equipment is according to plan if each of the requirements are met. The state of the monitored assets 810 is dynamically assessed, for example.

Asset location 820 is monitored as well. For example, Day View determines the process implication of an asset's availability at a designated location at a designated time. Extending the example used in asset state 810, a specialized piece of equipment required for a surgery must be in the operating room. A Boolean indicator of whether an asset is or is not in location as well as a degree or rate of being in the designated location in a future time may be provided, for example.

An illustrative example is an operation beginning in one hour. Specialized equipment is required for the operation at that time. However, the equipment is currently being sterilized. Based on timing information, the equipment's estimated time to sterilization is deemed sufficient to become sterilized and transported to the designated room within an hour.

An asset's dynamic metrics 830 may also be used by the Day View system, for example. Examples of asset metrics include an oxygen saturation from pulse oximiters, status codes from equipment, consumption profiles dispensed in anesthesia delivery, etc. Day View utilizes this information for availability and anticipatory forecasting, for example. An example of anticipatory forecasting is use of biometrical data from an operating room to assess progress relative to a protocol in order to assess a rate as in the asset location 820 illustrative example discussed above. For example, anticipatory forecasting may be used to determine if a surgery with complete within the next hour.

A dynamic view of a process and status of interdependencies is provided 840 with a comparison of what should be happening versus what is happening, what is about to be happening, and/or what is scheduled to happen, for example. Enabling assets that are missing through location, rate, and/or state are highlighted to process stakeholders in the form of 'satisfactory', 'warning' (pre-emptive action is required) or 'danger' (schedule will not be met and alternations to it are required), for example. While "satisfactory" "warning' and "danger" are utilized to illustrate the principle, other context appropriate designators may be used.

A plurality of modes may be used to view a scheduling process in accordance with certain examples. Four primary viewing modes including "what-was", "what-is", "what-will-be", "what-if". "What-was" 850 is a replay of activities, interdependences and risk levels as the process actually experienced. "What-is 860 is a view into what is happening in the process at the time of being viewed along with the current interdependences, states of assets, people and process risk. "What will be" 870 is the process in the future if the trending of "what-is" remains. "What-is" may be analogous to a radar on a vessel looking sufficiently far enough out over the horizon such that corrective action may be taken. "What-if" 880 is a scenario-based view to aid decision support. Alternatively, "What-if" can be retrospective to evaluate the likely outcomes had a "what-if" decision been made instead of the actual historical one.

In each of the four views, an objective is to have better process outcomes via reduction of controllable variation. Decision support may be provided to process stakeholders through the views, for example.

Figure 9:
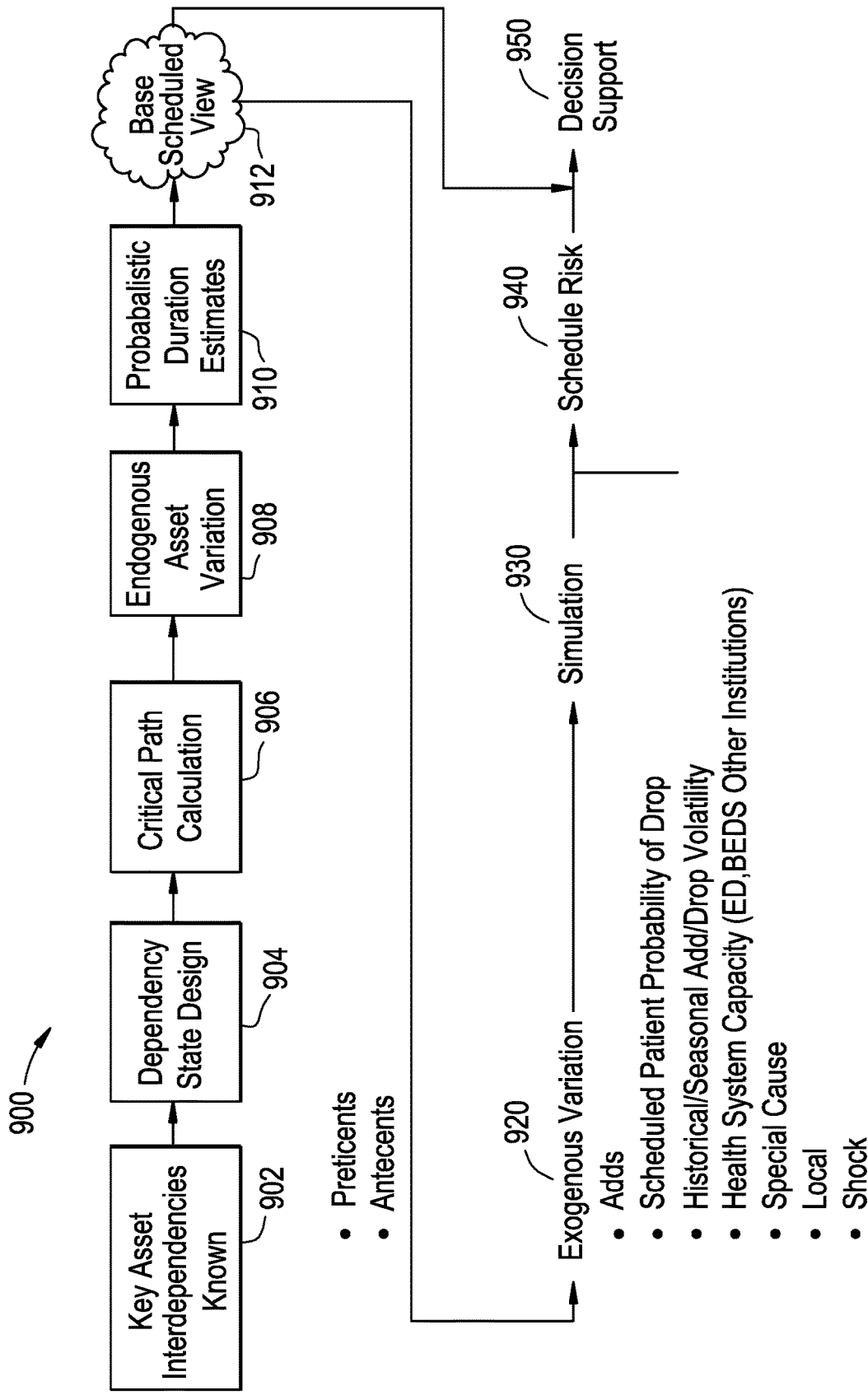
FIG. 9 depicts an analytical roadmap to build decision support using Day View in accordance with embodiments disclosed and described herein.

An analytical roadmap or workflow to build decision support using Day View is depicted in FIG. 9. A Day View is constructed from, for example, eight analytical steps which begin with identification of task(s) and asset(s) of process interdependencies; measures of availability; calculation of critical path; and use of exogenous variation, probabilistic duration, availability and reliability to calculate via simulation or math programming a probability of events beginning and ending at scheduled times or conversely, the start and complete times to achieve a designated probability estimate, for example. Asset interdependencies and dependency state design may be determined along with critical path calculations. Variation in items such as reliability of equipment, attendance record of staff, etc. may be factored in along with a probability duration estimate to determine a base schedule. The base schedule may then be simulated with a schedule risk. Decision support may be initiated to intervene in the process.

Key interdependencies are identified around consumption and utilization of assets (see, e.g., FIG. 10) in a process. These interdependencies are captured using a critical path method (CPM) transfer function technique 901. Critical paths are calculated using method known in the area of management sciences. Critical path and process slack times are made explicit via calculation and display, for example.

For assets most likely to become on critical path and potentially delay or cause bottlenecks in a critical path within the forecast horizon, monitoring is enabled 904 along metrics to measure availability, readiness and state, for example. An actual critical path is calculated 906 knowing the structure of interdependencies and state of the assets in the process using Gantt and CPM methods, for example.

Certain examples help provide a degree of robustness or tolerance of a schedule to variation. PDF's of endogenous variation from equipment availability and reliability of staffing and patients 908 are used with probabilistic duration estimates 910 and exogenous variation 920, such as adds and actual or likely drops to the schedule as well as historical volatility (e.g., factoring for seasonal variation and capacity) are used in a multi-modality simulation 940 to calculate duration probabilities of scheduled tasks being completed. The simulation engine 940 is repurposed for decision support to run "what-if" scenarios, for example.

Figure 10:
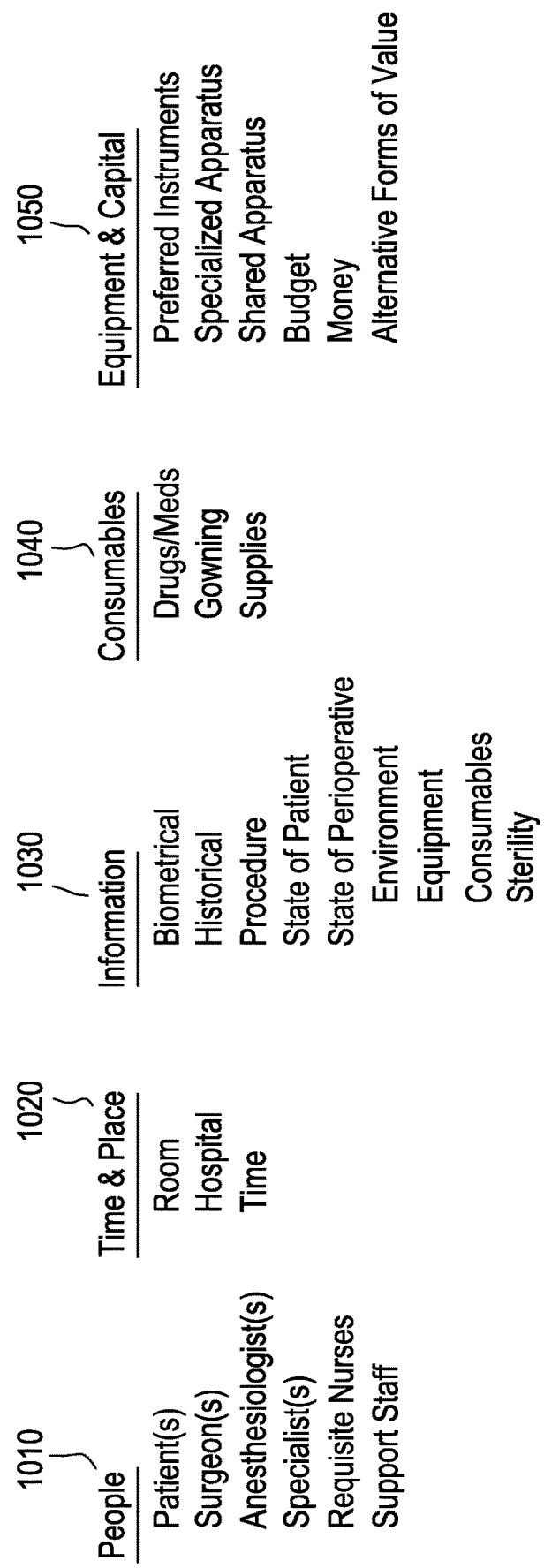
FIG. 10 illustrates exemplary assets capable of use in a Day View scheduling process according to embodiments disclosed and described herein.

FIG. 10 illustrates exemplary assets capable of use in a Day View scheduling process according to certain examples. Assets are items of value that can be used by the process. Assets include people, time and place, information, consumables, equipment and capital, for example. Assets can be used or consumed. Assets typically have availability and often reliability variation. In certain embodiments, asset availability and reliability are estimated initially from judgment and then from actual history. Probabilities for availability and reliability are then calculated for a new or forecasted context using (from history) observations made from a similar context at a singular operation or from a plurality of institutions.

Figure 11:
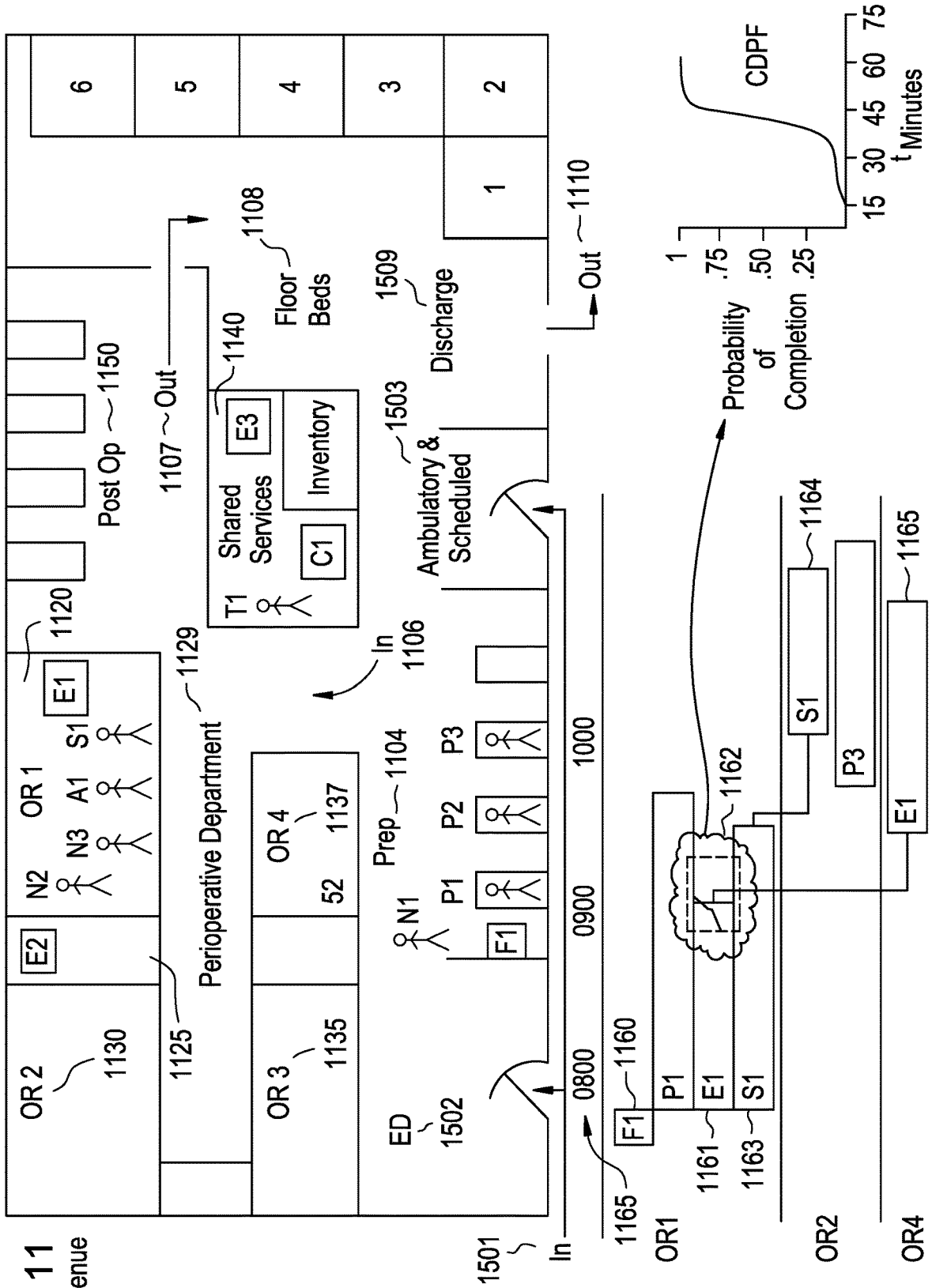
FIG. 11 illustrates clinical process management and value according to embodiments disclosed and described herein.

FIG. 11 illustrates process management and value according to certain examples. Delivery of healthcare services is used for purposes of illustration only. Hospital location and perioperative services are used to describe features, although the venue can be any clinical venue such as another department in the hospital, an ambulatory clinic, doctor's office or ward set up on a temporary basis such as for emergency or conflict. A cohort may be one or multiple institutions. A venue can be in domains outside of healthcare and include any ordered sequence of activities or use of assets that comprise process and schedule. An illustrative venue is a perioperative suite with flow into and out of up and downstream processes. Certain assets of the process are used, and the relationships of probabilistic duration, availability and reliability are used to aid in the explanation of methods used to calculate process risk.

FIG. 11 illustrates a clinical process managed according to certain examples. As shown in FIG. 11, operating rooms and other facilities do not exist in a vacuum. There are inputs and outputs to each scheduling process. Bottlenecks and variation may be introduced because, for example, even though a surgeon may be available for a surgery in one room, that room may be behind schedule due to post-op delay from a previous procedure or a lack of beds in recovery. Assets, durations and interdependencies may be reviewed to determine a cumulative probability distribution with all interdependencies for the delay and associated probability of completion. The schedule may then be stretched and/or shrunk to meet acceptable tradeoffs for necessarily operations during that day.

Patients arrive 1101 through an emergency department 1102, or walk in to receive emergency or scheduled services 1103. Live patients are discharged after clinical services are rendered 1109 and leave the hospital 1110. Within the clinical process, many departments provide clinical services and each benefit from Day View scheduling, for example. For illustrative simplification, a clinical workflow in and supporting a hospital preoperative department 1122 is considered.

Patients having surgery are either scheduled or are presented for surgery in an emergency. Scheduling of surgical services is typically made between a surgeon's or physician's office and a hospital according a surgeon's allocated blocks of time 701. Surgical procedures are scheduled days, weeks or even months in advance. Emergency procedures are not scheduled and, if reserve capacity is now available, emergency add-ons to a schedule constitute a significant source of variation. It is not always possible to set aside reserve capacity.

Patients are prepared for surgery 1104. Sometimes, patients are biometrically prepared for surgery and have documents or information such as lab results in preparation for surgery prior to the scheduled starting time. Examples of being prepared include being in a surgical preparation area (such as patients P1 and P2) and having blood pressure, heart rates, blood chemistries, and digestive chemistries within protocol and surgical permissions. Dependencies to be satisfied before preoperative surgical services can commence may be monitored. For example, if forms 1160 must be signed at least 15 minutes prior to surgery, staff may be alerted with sufficient time to complete the task prior to the schedule surgical start.

For illustrative purposes, suppose that a specialized piece of equipment E1 1161 in operating room 1 (OR1) 1120 is needed in OR4 1137 in one hour 1165, and E1 is needed in OR1 in 15 minutes 1161, or the OR1 surgery cannot commence. Likewise, the surgery schedule in OR4 in one hour and 15 minutes also cannot start without E1 1165. Further, with respect to a protocol step using E1 for patient P1, the person scheduled for surgery in OR1 has a 65% probability of being finished within 45 minutes, an 80% probability of being done within 50 minutes and a 98% probability of finishing within 70 minutes 1162. Furthermore, surgeon S1 is scheduled to report to OR2 1130 for patient P2 in two hours 1164. If signature of form F1 1160 is delayed, E1 1161 is on critical path because OR4 1137 may start late. Should F1 not be signed until 08:15 hours 1165, OR4's schedule risk is 35%, which is derived from knowing E1 is critical path and its probability of being used and released in 45 minutes (the original one hour minus 15 minutes delay) is 65% (1162), all other factors are satisfactory. If OR4 1137 is not on critical path, then this delay is an annoyance, but not critical as yet. However, note that surgeon S1 is scheduled to start OR2 1130 at 09:45 hours (1165), and that if F1 1160 is not signed until 08:15 hours (1165), that F1 and S1 are now critical path. The Day View Logic may generate a "yellow" alert to nurse N1 to review and have signed F1 at 07:45 hours, for example. The status of F1 would transition to 'Red' at 08:00 hours if the forms remain unsigned because of the S1 dependency on OR2 1164. As can be appreciated, combinations between numbers of rooms, patients, staff, equipment and information follow Powers Law.

Extending the illustration in FIG. 11, E2 1125 is a shared device between OR1 1120 and OR2 1130. It should be located between the rooms and be operational.

The Day View system monitors these dependencies 810, 820, and converts protocol 802, rules 803 and schedule 8018 into critical path logic 906. Variation simulated risk 930 is derived 1162.

Thus, in certain examples, a scheduling process includes a dynamic flow of people, assets and information. In the above example, once surgical procedures are rendered 1122, the clinical workflow moves patients into a post-operative (post-op) area 1150 for recovery and observation/stabilization. Patients are then removed 1107 to floor beds 1108 or discharged 1109, for example. If post-op 1150 or beds 1108 have no capacity, then the dependent antecedent processes are impacted. Day View provides visibility to upstream and downstream processes using the method illustrated above for OR dependencies, for example.

Shared services, such as nursing, surgical instrumentation, equipment technologists and cleaning are scheduled and/or called-for tasks. Availability and capacity constraints impact dependent processes. Illustrative examples include a nurse calling in to be absent from an upcoming shift, a surgical case cart not correctly inventoried, or a cleaning technician occupied in one room as another room is requiring clean-up. A ripple effect of these variations increases process variation. This process variation increases as discrete randomness accumulates.

Day View provides not only a system for identifying causes and effects of variation, but also a mechanism to help recover from unanticipated variation in a data driven and visual way, so as to facilitate conversation, ideas and buy-in of process stakeholders.

Day View may be configured to accommodate increasing degrees of exogenous variation and process objectives. For example, the Day View system may be configured to accommodate cases added to an already full schedule, as well as accommodate concurrently scheduled procedures that finish early and/or late. Process stakeholders help determine where to place new cases, what cases to postpone, which staff to add, redirect or drop, which rooms to shuffle, how to ration equipment, supplies, etc.

Certain examples use simulation to explore potential feasible solutions. For example, four modalities of simulation are employed to forecast asset and resource utilization assumptions. These four exemplary modalities are agent based simulation (AB), discrete event simulation (DE), continuous or system dynamic simulation (SD), and Monte Carlo simulation (MC). A critical path method (CPM) may also be repurposed in a simulation-based mode in that CPM is used to calculate critical path, probabilities of completion, and availability and feasibility of a solution.

Figure 12:
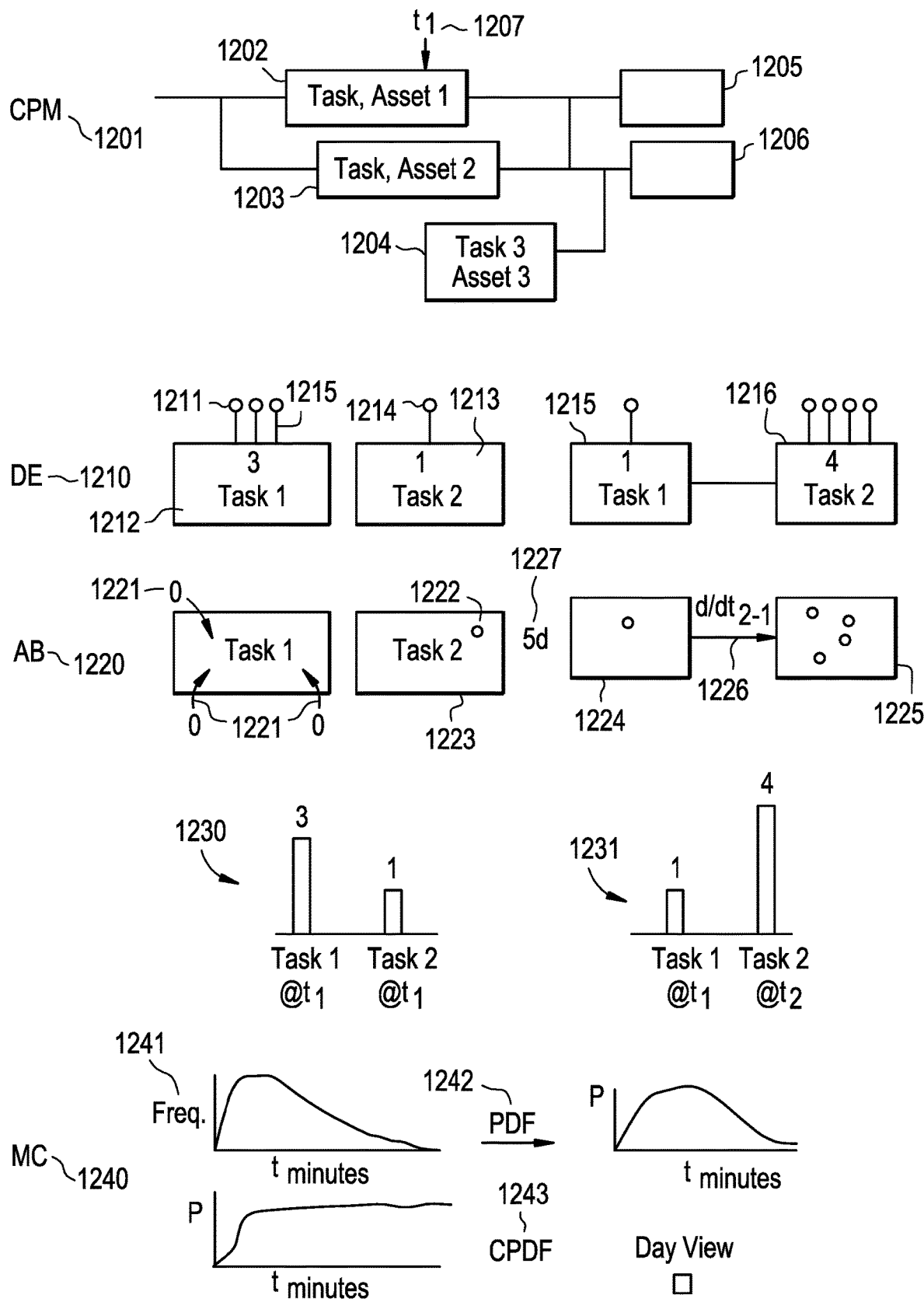
FIG. 12 illustrates dynamic system context and interaction between a variety of simulation and forecast modalities in accordance with embodiments disclosed and described herein.

FIG. 12 illustrates dynamic system context and interaction between a variety of simulation and forecast modalities in accordance with certain examples. Different simulation and forecast modalities may be utilized, for example. Critical path methods and forecast modalities may be utilized, for example. Methods such as CPM, DE, AB, MC, and/or continuous, differential or system SD, may be used. Historical observations may be organized in the form of a histogram and transposed into a probability density function and a cumulative probability density function (PDF) for incorporation into the CPM logic and as assumption feedstock for the simulations, for example. Differences between DE and AB in terms of process structure being known (e.g., scheduled) with DE or emergent with AB are illustrated, for example, in FIG. 12. How AB can be encapsulated by SD and the stock and flow of SD can be inferred from AB is illustrated. Using a number of different simulation modalities concurrently to solve forward-looked aspects of a schedule is used to determine what will happen during the day, for example.

Referring to FIG. 12, an interaction of simulation modalities is described. The ordering of tasks in a given schedule is not random, but, rather, is meant to extract maximum or improved utility from assets of a process to achieve one or more process objective(s). The CPM 1201 is one such method to identify and organize interdependencies in a way that enables feasible solutions. The CPM, while novel in its application to dynamic scheduling environments in healthcare operations, has drawbacks that diminish its utility when used in isolation without the benefit of the methods disclosed herein. CPM assumes that tasks will be completed as scheduled. Practically, this is seldom the case in dynamic environments. Thus, the believed critical path is but one instance of thousands of potential scenarios, some of which alter the tasks originally thought to be on critical path. A first extension of the critical path method is to utilize multi-modality simulation to draw path-independent probabilities or duration into the assumed task lengths. Additionally, equipment and personnel availabilities are incorporated as well.

The presently disclosed methods and systems are differentiated from Gantt and Program Evaluation and Review Techniques (PERTs) that replace deterministic duration assumptions in CPM with task duration probabilities. Certain examples not only draw from a static assumption of a probability distribution function such as Gantt but also provide duration probabilities from coupling to a simulation of the physical environment. Thus the CPM or PERT method is enhanced with a most recent actual duration that is observed within the hospital's or other clinical environment's operations from protocols that are tied to the specific care pathways for each patient and also an added precision of dynamic forecasts of duration that result from incorporation of process signals and activities on a dynamic basis into probability assumptions feeding CPM/PERT.

For illustrative purposes, Task1 1202 is, on average, 1 hour in length and completes with 95% probability in 90 minutes. The current art utilizes a single number for duration, typically, the mean or mode. Therefore, nearly half of the time an early finish is realized and half time, a delay is caused. If the delay is a critical path item, other procedures, staff, assets and patients are negatively impacted.

A schedule risk is estimated by converting historical observation of similar task and context durations 1241 into a PDF 1242 and integrating into a cumulative PDF 1243 using one or several simulation methods 1240, for example. Returning to the CPM for Task1 1202, task and total schedule risk are calculated along a full enumeration of path independent values for time assumptions of tasks. The method allows for an assessment of a given schedule's likelihood of completing on schedule, as well as for any selected time or probability. In this way, a schedule may be adjusted to complete with "50% probability", "80% probability", "95% probability", and/or any other desired likelihood.

Alternatively, a schedule can be made, and a likelihood of any task being completed at a given time can be expressed in a probability, such as OR3 will be ready for surgery at 1430 hours with 85% probability and at 1500 hours with 95% probability.

Tasks are interdependent on people and assets. Path independent assumptions, though superior to static scheduling, may not be sufficient to determine if a given person will in fact be available. An independent assumption assumes that resources required for a task will be available. Certain embodiments of the CPM method disclosed herein call assets of a process as though the assets were tasks and triggers alarms accordingly if double booking or a selected critical path risk is exceeded. However, certain embodiments employ more specific treatment of resources required for tasks through use of discrete event and agent based simulation.

Discrete event simulation 1210 is an ordered step-through of determined tasks 1212, 1213 in discrete time increments. At each time step, designated resources used for the task(s) at hand are attached 1211, 1214. Should concurrent tasks involve the same resource(s), logic 1215 is called from the simulation to determine which task has priority and which release rules apply once a particular resource is attached to a particular task. Thus, it may be possible that a single resource can serve two or more tasks and not be mutually exclusive as the way CPM is broadly configured.

Agent-based simulation 1220 assumes that the resources 1221, 1222 contain a prioritization rule set and respond to the surrounding environment. By studying how the resources (agents) respond, a structure of the system emerges. This is in contrast to Monte Carlo 1240 that is configured with a path independent assumption and linear or formulaic correlation that assumes the simulated task is much the same as its historical assumption set 1241. Monte Carlo determines a system structure from historical assumptions and from discrete events in ordered tasks and logical call of assets or resources.

Dynamic processes with interdependencies, randomness and human judgment defy any singular simulation modality. Certain examples utilize a multi-modality approach to asset utilization so that a scheduling structure enabled with the CPM method can be made more accurate and yet preserve the benefits of the visual logic CPM 1201 communicating in an intuitive, rapid, systemic form.

Continuous or system dynamic simulation 1227 is yet a fourth modality and is employed by the Day View scheduling system to assess "stocks", "flows" and "feedback structure" dynamics in order to assess process tendencies and policy impact. While process objectives are often related to capacity, throughput and timeliness, there are also strategic objectives that are often met or missed—not in a single shift, day or week, but over time. Examples include staff skill, "burnout", staff turnover, reputation, capacity to serve, and financial operating margin. This class of objectives shares the property of accumulation. For example, "skill" is a stock that may increase with exposure to different and/or frequent procedures. "Skill" may also erode through memory and/or dexterity loss from infrequent exposure or training. Similarly, a clinical workflow policy that schedules finish times at an expected value (the $50^{th}$ percentile) will result in near daily, if not hourly schedule misses and, resultantly, a disruptive, chaotic, stressful work day for the process stakeholders.

Occasional days of chaos are typical in all domains wherein scheduling exists. Related stress from schedule chaos, unanticipated variation, emotional decision making, unplanned overtime and the like will accumulate and, for some staff, will exceed a preference or indifference point causing the staff to seek other employment. A dynamic of new hires is that they do not have departmental knowledge, relationships and trust built due to a lack of history, context and/or requisite competencies. Existing staff are then encumbered with training the new staff. Thus there is detraction from a department's ability to execute tasks when experienced staff quit and new (ongoing) replacements enter. Process variation increases with lower capability if schedule durations remain as before. Thus, other process objectives are desirable to attain and can be attained by policies and decisions executed on an hourly, daily, and/or weekly basis via the decisions made in the clinical workflow enabled with Day View.

Figure 13:
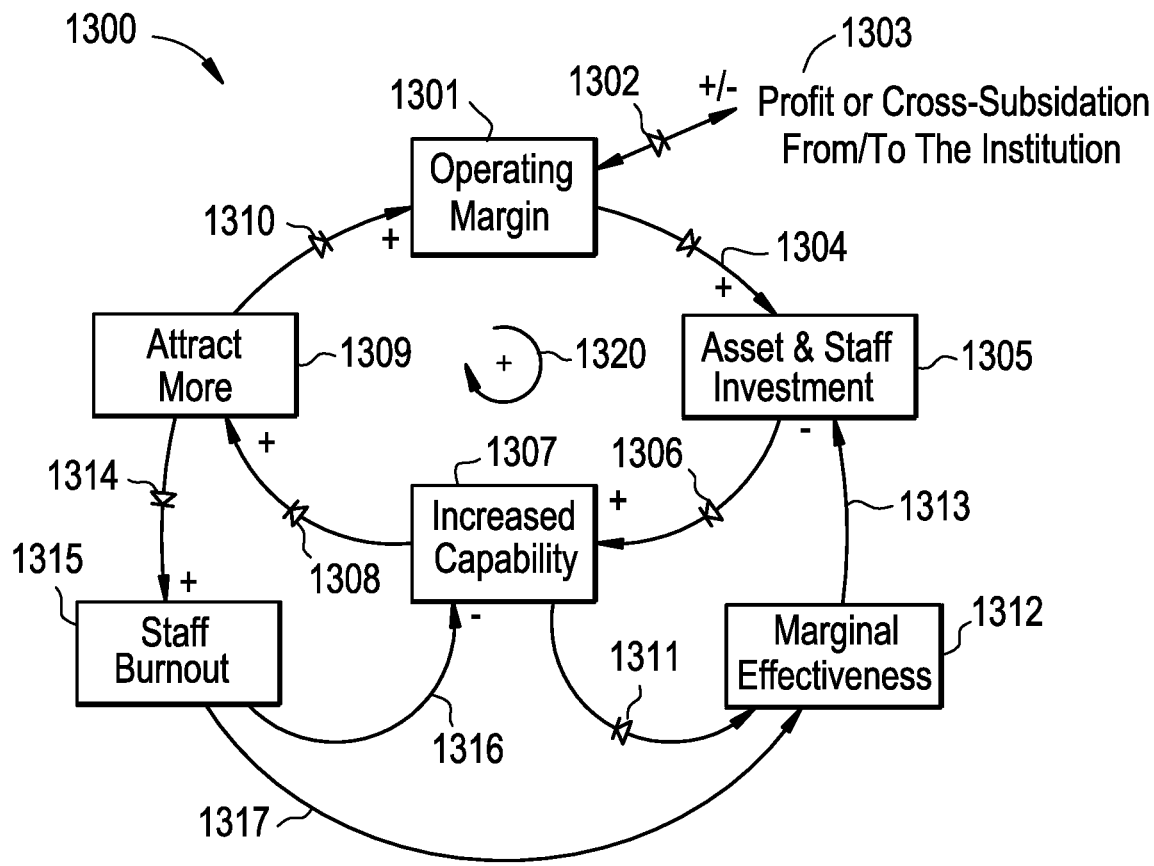
FIG. 13 depicts an example embodiment of an archetype structure for macro objectives according to embodiments disclosed and described herein.

FIG. 13 provides an economic, rather than throughput, view of a scheduled environment. A scheduling environment is a dynamic structure. An operator seeks to break even or have an account to cover a loss in operating margin 1301, for example. Assuming a margin exists, part of operating margin 1301 may be invested in staff and other assets. Hopefully, more margins grow results, but asset/staff investment can outstrip an ability to gain additional margin. Day View economic analysis may help to show a facility is not losing money by getting a better asset. Staff and equipment capability may be balanced with volume of patients/procedures to be handled. Variations may be caused by staff turnover, for example. Day View may be used to help accommodate variations without destroying any subsystem of the main system or burning out personnel, for example.

Referring to FIG. 13, an example of an archetype structure for macro objectives is presented. Beyond minute to minute, hourly, shift, daily, weekly, monthly, and/or other operational time constant within which tasks of a process are scheduled and work, there are typically additional process objectives to be managed and traded against as well as throughput, inventory, operating expense and ability to fulfill. These objectives may comprise scheduling and scheduling risk management methods. These macro objectives include budget, asset and staff investments, such as, for example, capitalized equipment, consumable stock, physical plant, staffing levels, staff competence and recruited staff. Having actual capability, capacity, and cost structure allow more effective use of asset and staff investments. An ability to attract more inputs into the system or adversely exclude entrants that the process system would not be advantageously suited to serve may be provided in Day View. Certain examples provide an ability to create economic value addition or an ability to meet financial targets, for example. A virtuous cycle that creates re-enforcing dynamics has dynamic counter forces and limits to growth. Attracting more entrants into the system than the system can sustain with expected or required service levels results in staff burnout or poor process outcomes. Over investing in capability whose cost cannot be liquidated result in financial loss that may not be sustainable. Served markets may not have sufficient volumes to sustain entrants into the process system built with an operating (and cost) structure that is designed for more (or different) volume. Certain examples allow process stakeholders to utilize both immediate process decisioning and policy and strategic decisions in such a way as to make informed decisions with probabilistic trade-offs.

Referring to FIG. 13, system dynamics simulation may be employed, and the structure of the macro system is such that it is desirable to operate a department with enough financial surplus or within budget that the department can improve itself, or at least maintain capacity and achieve effective outcomes. Operating margin 1301 is created by a surplus of revenues minus expenses. This margin may be invested in asset and staff 1305, paid to an institution, or deemed an allowed loss from the institution (wherein costs are netted out with a budget from the institution). Ideally, with asset and staff investment 1305, a department gains increased capability 1307, which would typically lead to capacity and reputation to attract more patients 1309 and therefore increase revenues, resulting in an increased operating margin 1301, assuming marginal revenues exceed marginal costs, for example. An ability to increase capability, lower cost and achieve more throughput comes from reinvestment 1305, and the cycle continues 1320.

In practice, there are endogenous forces that limit perpetual growth 1320. Should increased demand 1309 exceed capability 1307, a staff may become overextended or quit 1315, capability may diminish 1307, and fewer patients avail themselves of these services until demand abates to a level the staff can serve. Likewise, an overloaded staff and/or assets reduce effectiveness 1312 of asset and staff investment 1305. For example, a specialized asset for a certain procedure is obtained 1305 with intent to increase a department's capability 1307. However, staff, responding to process chaos, do not develop skill in the new competency and thus, the depreciating asset's costs are not liquated by revenue originally intended to be garnered by the investment.

Figure 14:
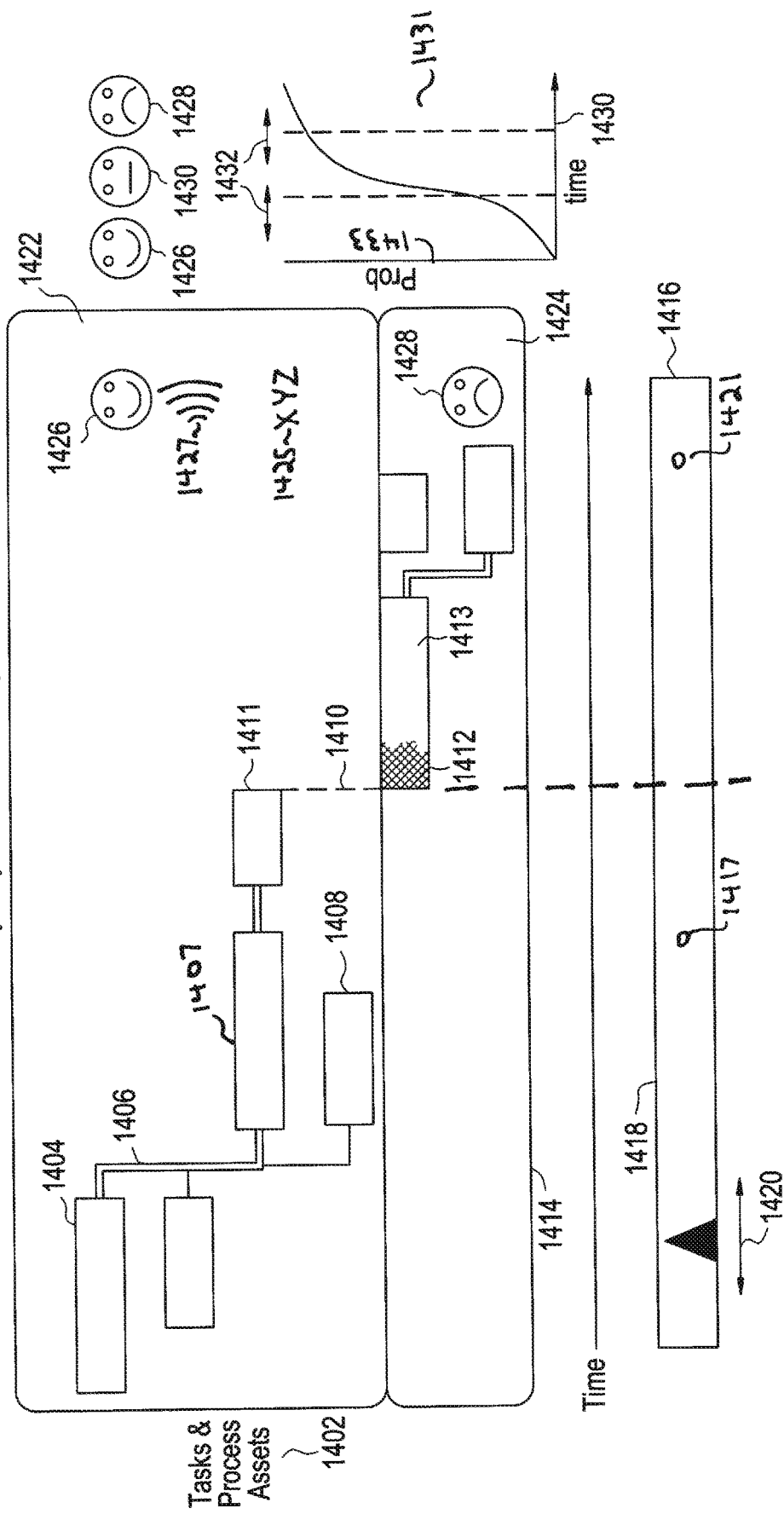
FIG. 14 illustrates an example of day plan forwarding and replay according to embodiments disclosed and described herein.

Referring to FIG. 14, an ability to play the day plan and/or schedule forward, an ability to replay the day as it was scheduled and/or emulate it as it actually occurred, and an ability to view a summary indicator as to the overall process state are explained. The assets of the process and their tasks 1402 are explicitly mapped as to their interdependencies, as has been discussed above. The relationships between tasks are not equal relative to their impact upon the schedule; some tasks are able to be the limiting factor in completing a schedule on time while others are not as they do not have interdependencies. Task 1404 is on the "critical path" 1406 while task 1408 is not. The clustered set of activities associated with a subsection of the day, such as an operation scheduled for a given room, are managed intensely. One operating room 1422 may impact another 1424 operating room's schedule in that task 1413 can not begin until task 1411 completes at 1410 since the same surgeon, for example, is involved. The risk of a late start is calculated from the methods and systems already discussed above and is visualized at 1412 for the attention of process stakeholders. The visualization may also be summary in nature, such as a red/yellow/green indicator or a "happy face". The summary indicators, 1426, 1427, 1428 enable the rapid scan of hundreds of activities such that the tasks involving intervention to keep to the schedule can be addressed while the rest of the system remains on schedule. The setpoints 1432 that transition from one process summary state to another can be deterministic or probabilistic 1430. Deterministic settings are rule based such that if a schedule is now late or if a downstream task such as 1413 to 1411 is to be impacted for a given duration, a happy face may turn from a smile 1426 to a frown 1430 to a sad face 1428 depending upon the setpoints. Probabilistic summaries take better advantage of the present invention's analytical method in that a scheduled task in the future may not start because of the present delays and/or the accumulated probabilities of delays building throughout the day. However, the future task may also start on time if things go well between now and then. A CPDF transformation is used to trigger the state summary and the transitions are adjustable 1432.

An ability to play the day forward is an improvement to the art of service-oriented processes. Prior to the start of a shift, for example, the day's schedule is advanced through time 1414 by adjusting at 1420 the virtual time 1418, such as by a slider bar or dial, and watching the schedule unfold along with the relative risks of delays or early completions of the assets of the process. In this way, the staff can be cognizant of the sensitivities and key risks to the schedule and can be additionally alert when risks increase to the key points. Likewise, a day can be replayed for study or training of decision support algorithms. The replay can be historical and/or comparative to what was planned or even what the scheduling algorithm chose as a robust path forward but was not necessarily selected.

In certain examples, information may be provided using a kiosk or workstation. Kiosk screens may be displayed with schedule, planning and/or decision support information, for example. A clinical workflow may be facilitated using input and output provided at the kiosk. Kiosk screens and information may be used to driving a clinical scheduling process.

In a perioperative suite, for example, a whiteboard, one or more computer terminals (e.g., Microsoft Windows-based and/or green screen computers), and/or one or more flat panel screens hung on the wall display activity in different rooms. Color may be used to show whether or not operations are proceeding according to schedule. In certain embodiments, a decision support window may sit or pop up on top of an application running graphics on a screen.

Certain examples provide a method to augment the decision support systems and methods disclosed and described above. In certain examples, stakeholders (e.g., doctors, hospital administrators, nurses, technicians, and/or other healthcare practitioners) are enabled to rationally and collaboratively make workflow choices in healthcare practice. Certain examples automatically set state definition(s) of schedule risk to help achieve goals of a hospital, department, and/or other healthcare facility.

As shown in the example of FIG. 14, the "Day View" allows a user to play forward and replay a day's schedule. Using the interface 1400, a schedule is summarized with respect to a likelihood of completing the schedule in a range of time. A schedule can be a task 1404 and/or a sequence of inter-related tasks 1404, 1406, 1407, 1408, 1411 with an aim of completing the tasks(s) by time 1410. In actual operations, time 1410 may be specified, such as at a busy or otherwise meaningful point in a day (e.g., a shift change, etc.). Time 1410 may also be a point at which an immovable task 1413 if preferred to start. For example, the task 1413 may be a critical, time-sensitive surgery with resources that are highly constrained such as a specialized surgical team for a transplant or degrading patient condition. As another example, task 1413 may be a task upon which a chain of other workflows is dependent.

Through execution of tasks in a clinical process and the interdependencies of those tasks on people, processes, and other schedule demands (e.g., addition of tasks, reliability of supporting apparatus and/or information, etc.), tasks such as tasks 1404, 1407, and 1411, may finish before or after their scheduled starting or stopping times. Certain examples help to understand and respond to a probability of completion (e.g., of a sequence of tasks 1404, 14047, 1411).

A probably of completion of one or more tasks in a range of time can be represented as a histogram. The histogram can be fit into a probability density function (PDF) via one or more statistical techniques (e.g., empirical data analysis, distribution fitting and parameter estimation methods, goodness-of-fit tests, etc.) whose range describes a full spectrum of completion times and a probability of completing at a given time. The PDF is a function that describes a relative likelihood for a variable (e.g., task completion, etc.) to have a given value (e.g., by a certain time, within a certain duration, etc.). The probability density function may also be referred to as a probability distribution function.

The PDF may be integrated so that a cumulative probability density function (CPDF) is calculated via a statistical method such as theoretical closed-form computations or Monte Carlo, agent-based, and/or discrete event simulation, etc. While cumulative probability density function (CPDF) is used herein, this term may also be referred to as a cumulative distribution function (CDF) (or just as a distribution function (DF)). The CPDF describes a probability that a variable with a certain probability distribution (PDF) will be found to have a value less than or equal to a certain threshold or value.

As shown in the example of FIG. 14, a CPDF 1431 has a time duration 1430 and a probability 1433 which may be subdivided into regions 1432 of time duration. The CPDF 1431 is utilized to define a state of schedule risk. In a given healthcare environment, one or more states of schedule risk may be defined based on meaningful conditions for that environment. As an illustrative example, three states of schedule completion risk are defined: low, medium and high.

A low risk state is defined as a state in which task 1411 will complete by time 1410 on the scale of the schedule span 1416. A probably associated with the low risk state is defined as "low". A low risk state may be annotated graphically with a color (e.g., green, etc.) and/or text 1425, an icon 1426 (e.g., a happy face, etc.), sound 1427, etc. These indicators of schedule risk state change as a function of the designated schedule risk probability range set by adjustments in region of time duration 1432 on the associated CPDF 1431.

In the illustrated example, a completion of a task sequence 1404, 1406, 1407, 1411 with a probability, for example, of completion at 80% or higher (e.g., the PDF probability value) has a "low" schedule risk state. The risk state indicator 1425, 1426, and/or 1427 is then utilized to convey that operations are in good order with respect to the schedule and that existing workflows can proceed as-is.

In contrast, a completion risk, for example, of between 30% and 80% may be deemed to be cautionary. A corresponding "medium" risk state is then set with an indication of cautionary 1430 rather than happy 1426, for example. The cautionary risk state is set noting this cautionary circumstance with respect to an overall objective such as completion of clinical tasks within the schedule.

A completion risk, for example, of between 0% and 30% likelihood to be achieved by time 1410 may be set based on time duration sub-range 1432 to a "high" schedule risk state. A visualization of a "sad face" 1428 may then be provided rather than a happy face 1426 or cautionary face 1430, for example.

In certain examples, a probability of early completion can also be tracked and identified along with potential for late completion. For example, an operation might need to tie into a succeeding task or action in a time-critical fashion, and those downstream task(s)/action(s) might not always have the necessary resources available at hand (such as transplant operations, and/or other type of surgery being started and finished earlier than planned while downstream staff and units may not be ready to accept the patient). In such examples, because earlier completions may lead to undesired overall system-wide schedule risks, both tails of the distribution (e.g., tasks ending early as well as tasking ending late) can be marked as high-risk situations.

In certain examples, completion on a time span 1416 may fall in a range 1412 which impacts a task 1413 which in turn impacts a global objective such as completing cases for a given shift or day, avoiding overtime expense, achieving a service level agreement (SLA), etc. During a scheduled period 1418, if the schedule risk 1431 changes states according to an adjustable set point(s) 1432 corresponding to region(s) of time duration, then workflow(s), such as alarm(s), recovery process(es), specific call(s) to manage specific people and/or assets, etc., are triggered with an aim of bringing the schedule risk state back to a desired level.

For example, if patient A's anesthesiology or surgery is detected to be taking longer than planned, and therefore starting to put patient B's surgery schedule under elevated risk, then patient B's surgery could be moved to another location or be completely rescheduled to bring the overall schedule risk below an acceptable tolerance level. Such mitigating or corrective action may involve making many other ripple-effect changes to the schedule(s) of other directly or indirectly related object(s) in other parts of the perioperative areas or even the overall hospital including post-anesthesia care unit (PACU), intensive care unit (ICU), step-down and/or inpatient units. For example, if patient B is currently occupying an inpatient-unit bed in the hospital and was originally scheduled to move into the operating room (OR), followed by the PACU, then to the ICU, and finally to a step-sown unit, the hospital might end up with one less bed capacity in the current inpatient-unit but one more capacity in all the post-OR units because patient B's surgery might have been delayed by a few hours or up to a whole day. If patient B is en route or already in the emergency department (ED) pending surgery and this hospital finds out that it will not be able to accommodate him within an acceptable timeline due to a prior operation taking longer, then that patient might need to be rerouted to another hospital, for example.

To help maintain global or other high-level objectives for a healthcare facility, state transitions indicated by sub-regions of time duration 1432 can be set which in turn triggers awareness, decision support, and workflow(s) beneficial to maintain objective(s) and an acceptable schedule risk.

Figure 15:
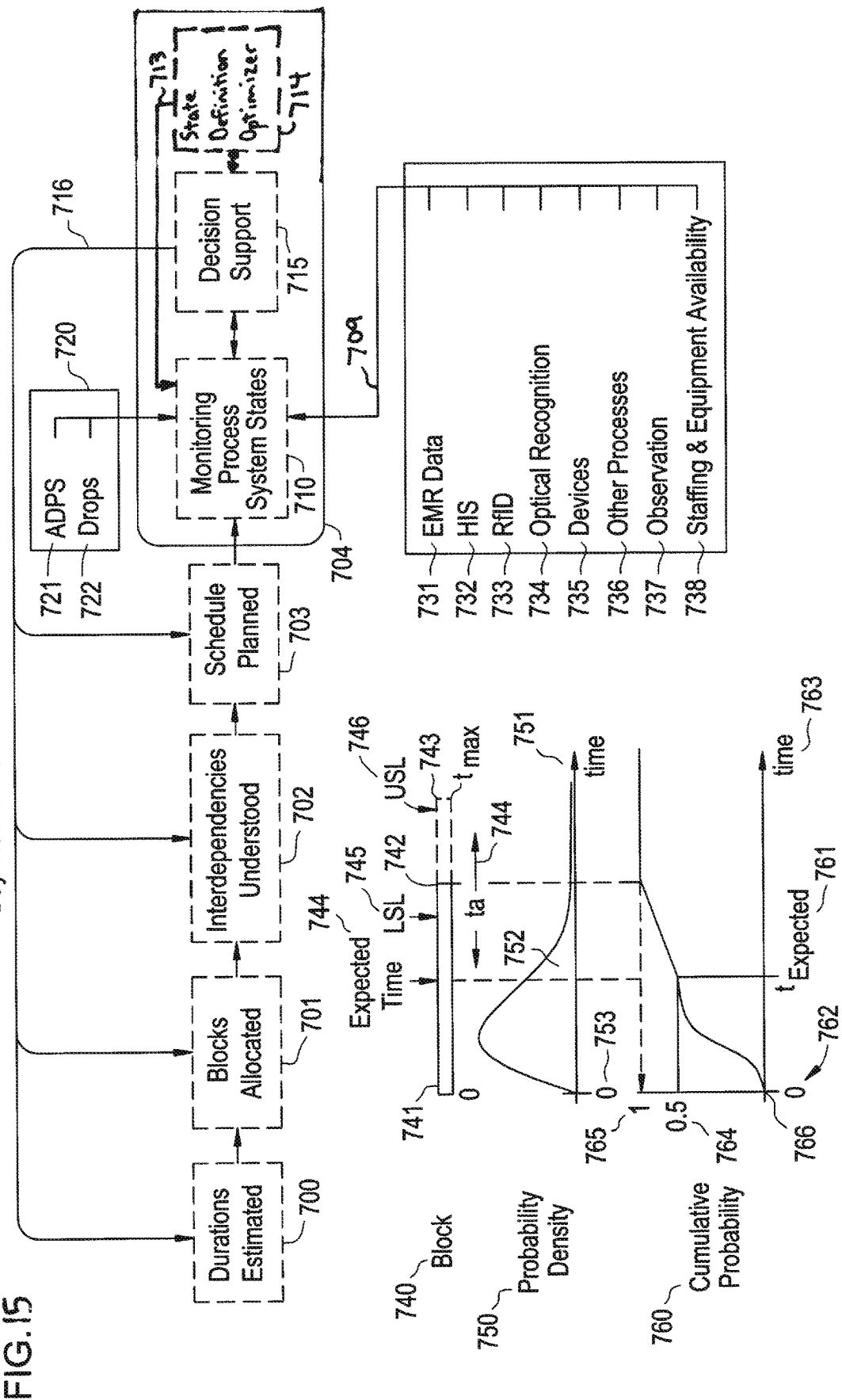
FIG. 15 provides an example process context of a "Day View" scheduler according to example embodiments disclosed and described herein.

FIG. 15 provides an example process context of a "Day View" scheduler. The example of FIG. 15 expands on the process context provided and described above with respect to FIG. 7. However, the process context of FIG. 15 introduces a state definition optimizer 714 which impacts decision support 715 and process operation.

As shown in the example of FIG. 15, the state definition optimizer 714 provides the set points 1432 to the process monitoring 710 via a feedback loop 713. The state definition optimizer 714 sets, for example, the upper specification limit (USL) 746 and the lower specification limit (LSL) 745 which divide time 1430 into schedule risk states. Workflow(s) are triggered 709 by the schedule risk state. For example, a workflow to expedite availability of staff, equipment, consumables, space, information, etc. can be triggered 709 in order to optimize or otherwise improve or maintain a schedule risk state.

The risk 1431 of task(s) completing changes through a day 1418. As shown in the example of FIG. 14, a total daily schedule risk 1424 and/or a specific task or sequence of tasks 1410, 1412 may be of interest to an administrator and/or other personnel involved in the process. The state definition optimizer 714 solves state changes 1432 for multiple view of time such as a task sequence or start 1410 and/or a day, month, hour, and/or moment of schedule duration 1416, for example.

In an example, schedule risk states are adjusted to help achieve departmental level objective(s) such as completing a clinical case load with staff overtime at less than two hours at a service level exceeding eighty percent (80%) likelihood at an end of a shift and a ninety-five percent (95%) likelihood at an end of a maximum overtime period. To achieve both service level and cost objectives, cases during progression of the case should not be allowed to propagate delays through interdependent people, tasks, and/or resources. Workflow(s) and awareness to eliminate dynamic critical path delays that can propagate, when targeted at eliminating preventable delays early enough in the process, can increase the likelihood of meeting the global objectives (of service level and cost for the department).

As shown in the example of FIG. 14, at time 1417, ahead of a service level target at 1410, a probability of case completion at time 1410 is calculated using one or more methods described above. A probability of case completion at a two-hour limit of time 1421 can also be calculated. Additionally, one or more state transition setpoint(s) at, for example, time 1417 can be determined to trigger corrective awareness and/or corrective workflow(s). The time 1417 represents, for example, a time in advance of a desired completion time, shift change, overtime limit, and/or other time of interest such as a desired start time of a critical task, etc. In an example, awareness can be configured to be "yellow" or indicate a warning (e.g., via a cautionary icon 1430) at a medium risk state, while a corrective workflow is triggered at a high risk state (e.g., corresponding to the sad face 1428).

Using time 1410 as an example of a time 1430 at which a desired completion probability 1433 is desired (e.g., an 80% probability) in the CPDF 1431, task risk thresholds or setpoints can be established at a time 1417 prior to the time 1410. At time 1417 in advance of time 1410, a task risk threshold can be set to generate an alert or awareness (e.g., via icon 1430 and/or associated audio 1427, text 1425, etc.), trigger a corrective/compensatory workflow (e.g., indicated by an associated icon 1428 and/or associated audio, 1427, text 1425, etc.), and/or perform other action by adjustment of the state transitions 1432. The graph of CPDF 1431 may correspond to a determination in time period 1412, for example. One or more times for completion and/or start of a task can be associated with a calculated setpoint (e.g., an optimized setpoint) and levels of satisfaction can be nested within each other in a desired and/or determined combination.

For example, returning to patient A and patient B discussed above, a risk of unavailability of a required operating room (OR) or post-anesthesia care unit (PACU) would be a very critical, and therefore highly undesired, risk, whereas a risk of leaving a very expensive OR under-utilized would be a risk of relatively lesser importance. Similarly, a risk of unavailable step-down or in-patient beds may be of lesser relative importance, and under-utilization of less expensive resources, such as an inpatient bed with rather basic equipment integrated around it, may be a least critical risk of all of these potential risks.

In certain examples, the state definition optimizer 714 uses a stochastic optimization technique such as meta-heuristic search, dynamic programming, etc., to adjust state transition setpoint probability(-ies) for one or more tasks so that, if turned from high risk to low risk, task(s) on a critical path will complete and enable departmental (and/or other high-level or global) objective(s) to be met at the specified probability(-ies) and time(s).

Figure 16A:
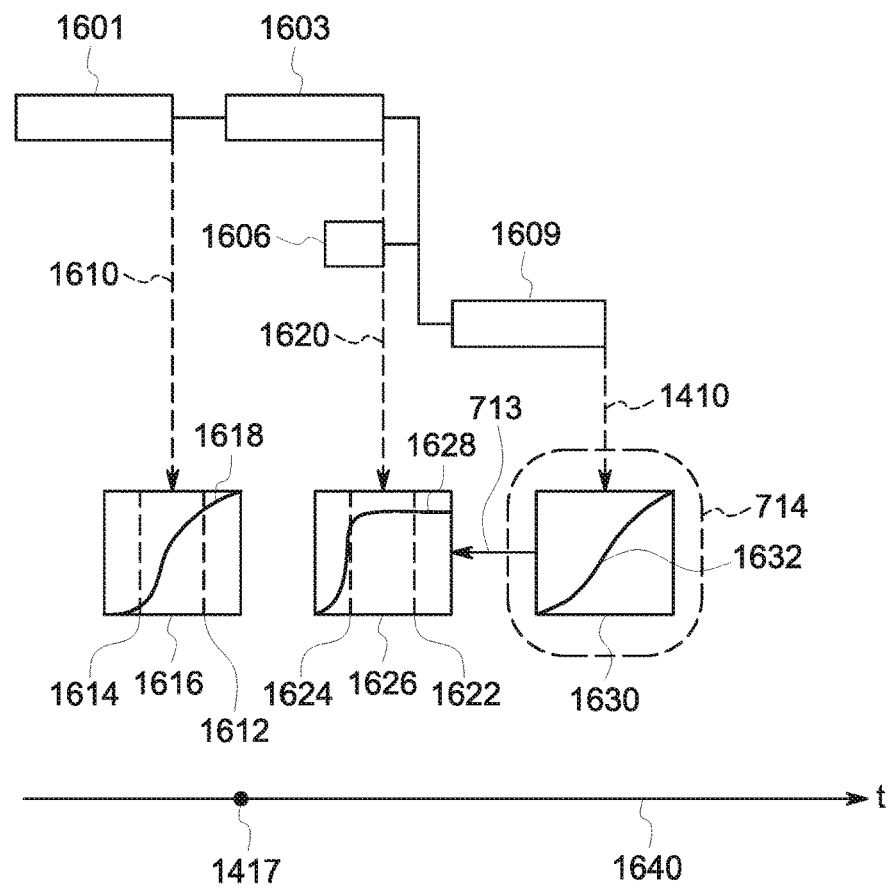
FIGS. 16A-B illustrate an example of state transition setpoint optimization in accordance with example embodiments disclosed and described herein.
Figure 16B:
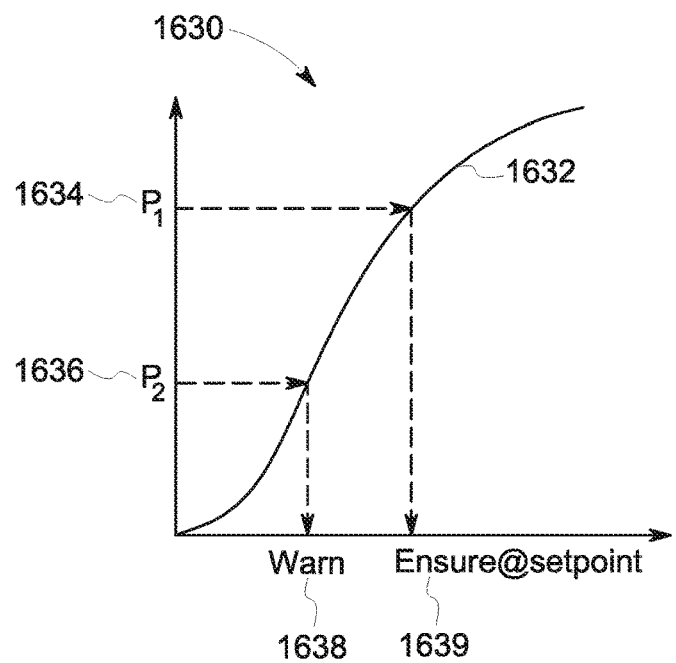

FIGS. 16A-B illustrate an example of state transition setpoint optimization. As illustrated in the example of FIG. 16A, it is desired to have a task 1609 complete at time 1410 on schedule time line 1640 with a probability P1 1634. To achieve this, critical path tasks 1601, 1603, and 1606 should complete before task 1609 begins. In the context of this example, a task may be a specific physical procedure, a case, a component of a protocol, etc.

In the example of FIG. 16A, at a given time 1417 before completion of the task 1609, there are risks to completing critical path tasks 1601 and 1603 according to a schedule. These risks may be mitigated (e.g., by awareness and/or corrective workflow) as triggered by schedule risk probability states 1616 and 1626. Each schedule risk probability state 1616, 1626 has one or more probability setpoints 1612, 1614, 1622, 1624 along a cumulative distribution function 1618, 1628. Probability setpoints 1622 and 1624 for task 1603, for example, are adjusted via feedback 713 by the state definition optimizer 714 to help ensure a warning 1638 (associated with a probability P2 1636) as well as a service level setpoint 1639 (associated with a probability P1 1634) are met for task 1609.

For example, as shown in FIG. 16A and in an enlarged view of FIG. 16B, a time constraint may utilize a cumulative probability distribution function 1632 to set a probability if time (e.g., overtime) is the objective. In the example schedule risk probability state 1630, the function 1632 may also be used so that the overtime may be met 1639 at a probability P1 1634 and schedule completed 1609 if the calculated probability is less than probability P1 1634, for example. A probability P2 1636 can be used to trigger an alert or warning 1638 prior to the ultimate object setpoint 1639. A warning and/or automated workflow intervention can be calculated using the same method.

Figure 17:
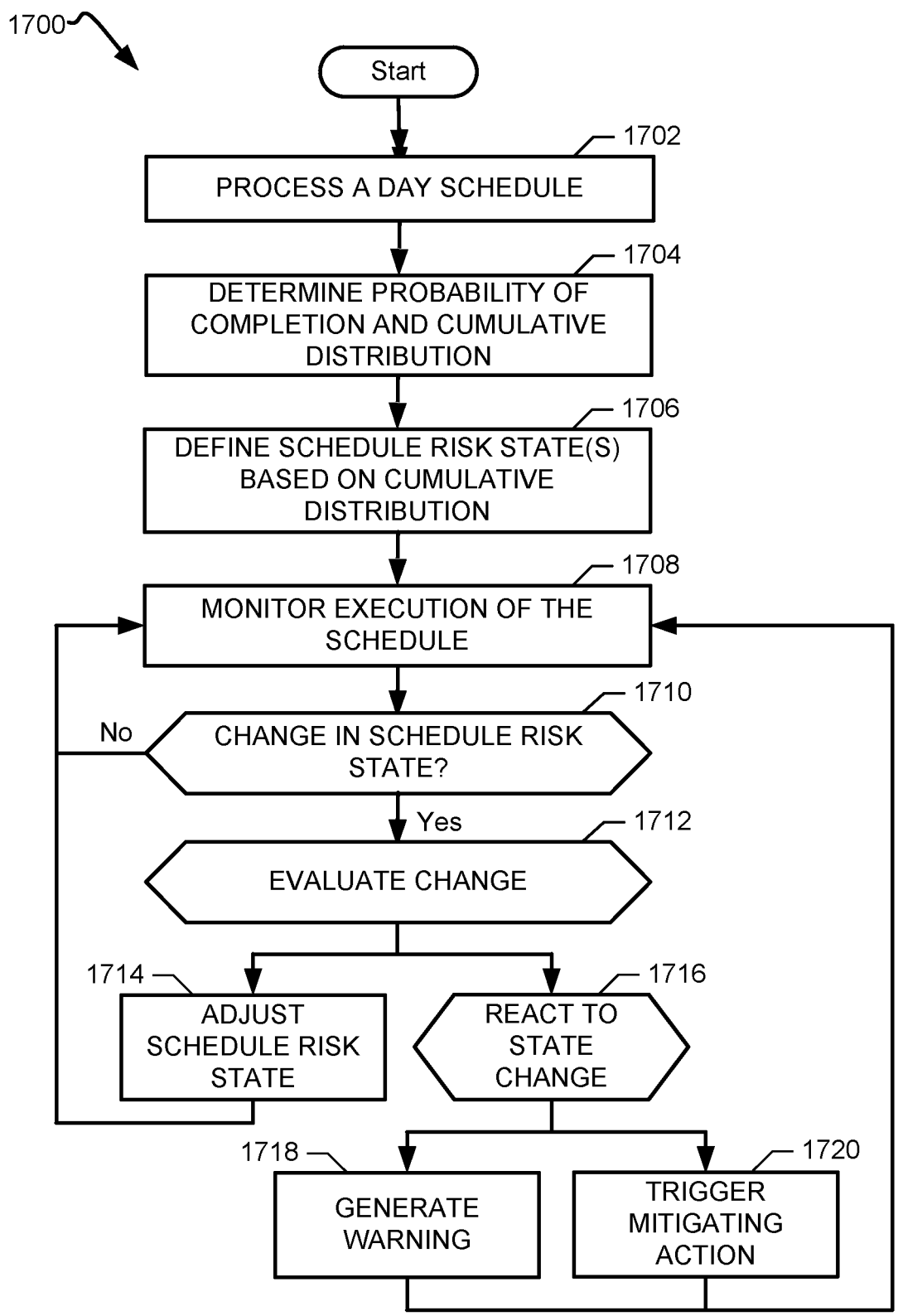
FIG. 17 illustrates a flow diagram of an example method to manage schedule risk state and set duration risk state transitions in accordance with example embodiments disclosed and described herein.

FIG. 17 illustrates a flow diagram of an example method 1700 to manage schedule risk state and set duration risk state transitions in accordance with presently disclosed examples. At block 1702, a schedule or plan for a day in a healthcare facility (e.g., a department, an office, a clinic, a specialty, a hospital, etc.) is processed. For example, an electronic schedule or plan is analyzed by the system to identify tasks, resources, times, durations, relationships, etc., involved in the schedule.

At block 1704, a probability of completion associated with tasks forming the schedule is determined. The probability of completion can be defined as a PDF and used to form a CPDF, for example.

At block 1706, one or more schedule risk states are defined based on the CPDF of completion/schedule risk for tasks in the schedule. Each schedule risk state may be associated with a duration triggering one or more setpoints defining a transition between states of schedule risk (e.g., from okay (low risk), to a warning (medium risk), to a mitigating action (high risk)).

At block 1708, execution of tasks in the schedule is monitored. The execution may be a "real-time" execution of ongoing events/tasks in the schedule and/or may be a predictive "what-if" look at the schedule going forward or a "rewind" or "replay" look at the schedule going backward, for example.

At block 1710, a change in schedule risk state change is determined. For example, if a task is behind schedule, resource becomes unavailable, a task is ahead of schedule, resource is available early, etc., a state of schedule risk may change. If a change is not detected, then monitoring continues at block 1708.

If a change is detected, then, at block 1712, the change is evaluated. For example, factor(s) contributing to the schedule risk state change can be evaluated. A degree of schedule risk state change can be evaluated (e.g., slightly behind/ ahead of schedule (e.g., within a tolerance or standard deviation), more than a threshold or tolerance behind/ahead of schedule, etc.). A circumstance of schedule risk state change can be evaluated. Based on the change in schedule risk state, a next action is determined. The next action can be based on the degree, circumstance, and/or other factor(s) associated with the schedule risk change.

At block 1714, schedule risk state can be adjusted. For example, if the degree of state change was slight (e.g., within a tolerance) and/or circumstances justify the change, then a definition of the schedule risk state (and/or adjacent/associated schedule risk state(s)) can be adjusted. For example, set point(s) defining the schedule risk states can be automatically moved by the system based on the processing of the schedule risk state change/transition.

Alternatively or in addition, at block 1716, a reaction to the schedule risk state change is triggered. For example, in response to the transition from one schedule risk state to another, a corrective or mitigating action such as a warning (e.g., a displayed icon, text, and/or audio), an altered/corrective/mitigating workflow (e.g., to move a patient, reschedule a procedure, reallocate resources, extend overtime, etc.), etc., is automatically triggered. As shown in the example of FIG. 17, at block 1718, a warning can be generated to alert a user to the state change and/or associated risk. At block 1720, a mitigating action can be triggered to attempt to correct the state change. Such action may be based on one or more forecasts and/or what-if simulations, for example.

After the change in schedule risk state is acted upon, the process 1700 can continue to monitor execution of tasks at block 1708, for example. Thus, certain examples move from a passive robust system to an active robust system using near-real-time prediction to provide active control and mitigation. The method 1700 can help provide management and optimization of elements such as patient flow, bed allocation, patient transfer, task resource assignments and priorities as well as healthcare workflow, process, and protocol. In certain examples, based on healthcare facility configuration, historical data, current state information, and known future events, potential problems can be forecast and mitigated.

For example, using systems and methods disclosed and described herein, today's forecast can be simulated to determine that if the schedule proceeds "as usual", a demand for cardiology beds is unlikely to be met. However, a number of alternatives can be simulated/emulated for testing purposes. For example, if additional staff is called in, will that affect the schedule risk state and likelihood of completion? Alternatively, what is the impact of opening additional cardiology beds? What if certain discharges are expedited? A number of informed "what if" scenarios may be tested and feedback provided to make an automated and/or user-informed decision regarding schedule risk state and workflow adjustment.

Figure 18:
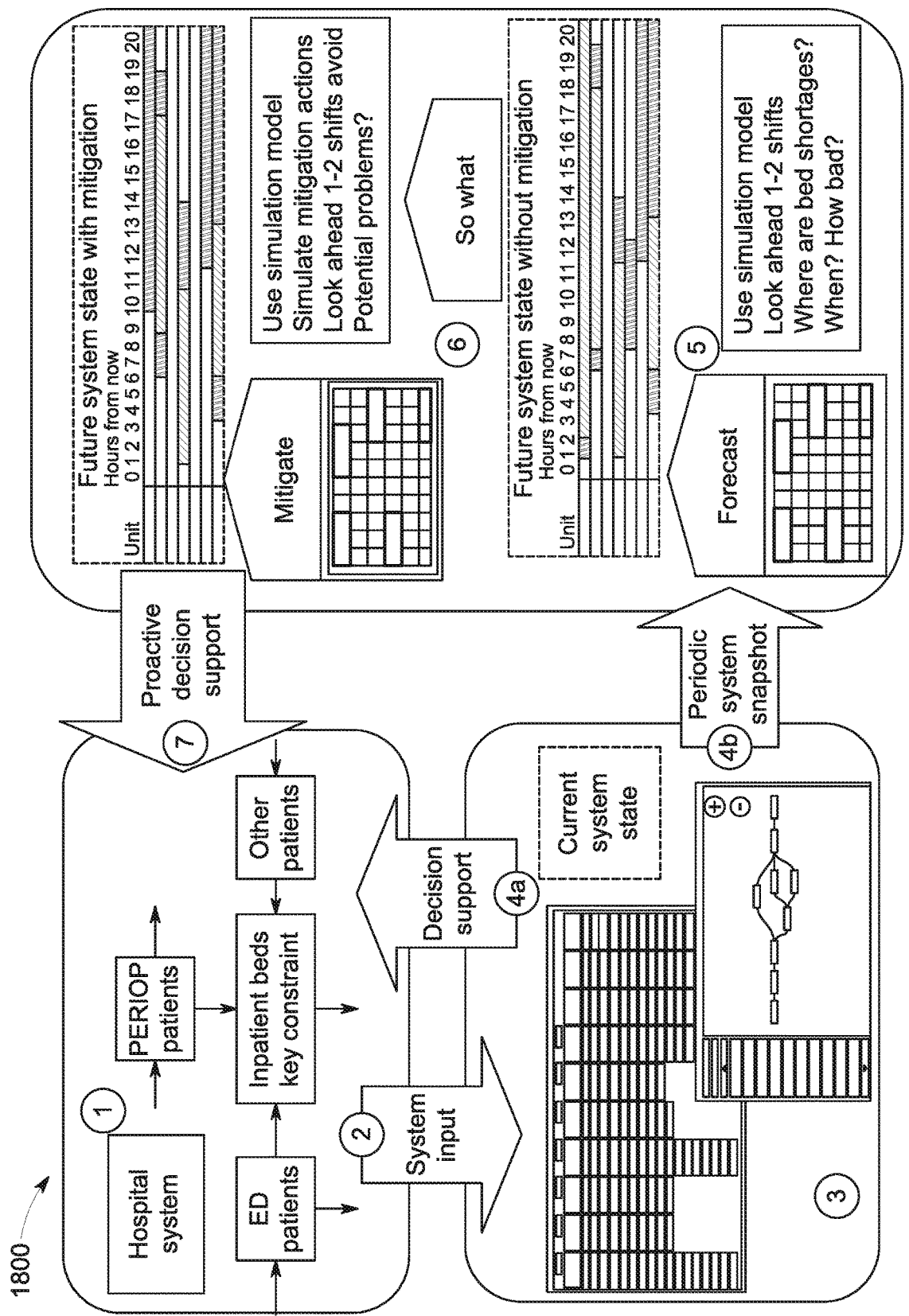
FIG. 18 depicts an example early warning and mitigation system used in accordance with example embodiments disclosed and described herein.

For example, FIG. 18 depicts an example early warning and mitigation system 1800 used to determine, based on PDF and CPDF, a likelihood of schedule risk state transition and strategy, based on the CPDF, to mitigate through proactive decision support. As shown in the example of FIG. 18, at 1, a hospital system provides information regarding perioperative patients, emergency department patients, and other patients occupying a number of available inpatient beds. The inpatient bed information is identified as a key constraint (e.g., a global objective). At 2, this information is provided as a system input to a current system state 3. Based on the current system state, decision support 4a can be provided back to the hospital system 1. Additionally, a periodic system snapshot 4b is provided to forecast 5 based on that system snapshot.

For example, using a simulation model based on PDF/CPDF, the hospital system schedule can be simulated 1-2 shifts into the future to forecast 5 where are bed shortages, when are bed shortages, how bad are the predicted bed shortages, etc. A future system state without mitigation can be forecast. Schedule risk state and a change in schedule risk state can be evaluated based on an LSL and USL for each risk state as determined based on information from the hospital system 1 current system state 3, and historical information.

The forecast 5 is then evaluated 6 to determine potential mitigation. Using a simulation model, mitigation action(s) 6 can be simulated to evaluate their potential affect 1-2 shifts into the future. Evaluation is performed to determine whether and to what extent, one or more mitigation actions are likely to avoid potential problems (e.g., based on CPDF and component PDF). An outcome of the mitigation simulation analysis is provided as proactive decision support 7 back to the hospital system 1. Thus, a closed feedback loop can be provided to provide traditional as well as proactive decision support to a hospital system.

Thus, rather than ignoring schedule risk and treating delays as an average value formed from durations shorter and longer than an average (or median) point estimate value, the presently disclosed systems and methods account for schedule risk and accommodation of delays in a probabilistic approach. Thus, rather than a deterministic view in which every variable has a value, a probabilistic or stochastic approach accounts for randomness and variability through probability distributions. For example, consider a schedule using average (or any other single number) duration for an inter-related task. In instances when an actual duration realized in a care delivery process is more than a point estimate used in scheduling, delays will propagate throughout the rest of the scheduled activities. In instances when the actual duration is less than the point estimate, there is underutilized capacity. A way to avoid the ripple effect of delays is to add buffer or "slop" or "slack" time into the point estimate, thus ensuring that there will be underutilized capacity. This underutilized capacity is hidden because clinical activities are reported to have been achieved by the scheduled end time. Conversely, enabling probabilistic scheduling and dynamic workflow in turn enables an informed trade off of conducting/fitting in clinical activities in the presence of variation in demand, task durations and interdependent asset availability versus excess (and underutilized) capacity which modern health systems can increasingly not afford to have.

Certain examples enable scheduling ahead of admission, during the hospital stay, and are anticipatory in nature, as a function of how a single patient's day is unfolding as well as how all supporting resources are being consumed by other patients. Certain examples can schedule services, tasks, people, assets, physical space, consumables at any point in time. Schedules can dynamically adjust schedules with a sufficient degree of precision in terms of time and resource specificity to function as a directive workflow engine as well as a scheduling system and can feed input into another scheduling system(s).

In certain examples a designated care plan is converted into medical protocols as defined by a standard of care. The plan's completions are dynamically managed to stay within a desired probability of being completed. Additionally, there is specificity for all interdependent resources involved to implement a care plan, including people, space, specific devices and consumables. For example, given a desired treatment protocol, specificity on task interdependency can be provided at the granular level of instruments, consumables, and/or prerequisites to calculate the ability to actually implement the protocol.

Certain examples then monitor asset, information, people interdependencies by task, as well as prerequisites of their use, and availability states. Using such specificity, one or more "what-if" scenarios may be formulated and run, for any time interval. As a state of any interdependent resource changes in real time or simulated forward time, dynamic probabilities of starting and completing on time are calculable. By specifying and tracking pre-requisites and interdependencies of tasks, assets, states of resources, states of the system and people, etc., certain examples enable what-if scenario and probability calculation of start and complete times, resource use and schedule risk for any scenario. By tracking pre-requisites and interdependencies between tasks, a state change in an interdependent task or resource can be identified and its effect on schedule and workflow determined at or ahead of real time.

Certain examples calculate a probability, consume a probability state, and make probabilistic decisions. Rather than building in excess capacity or "slack" in the schedule, schedule risk can be dynamically calculated at any point in the day or in the future. Certain examples also allow a hospital staff to set a dynamic threshold for schedule "goodness"—for example, the schedule is 20%, 50%, 80%, 95%, etc., likely to be on time at a given point in the day. Whatever the hospital desires to set as an acceptable risk is thus the determinant of a schedule or workflow being "feasible".

Further, certain examples facilitate replay of a day from many perspectives: task completion, from the view of a resource, and from the view of presenting feasible forward paths as they actually unfolded as the day progressed. Because explicit relationships are mapped between care plan, protocols, tasks, and resources, for example, actual circumstances of the past may be replayed and all interdependencies illuminated. Feasible alternatives can also be replayed. Using "what-if" capability, decisions may be reviewed and alternate decisions, in retrospective review, may also be made for training or shift turn-over purposes.

In certain examples, events of a day can be replayed from the perspective of a resource such as an asset. An example being a particular piece of specialized equipment—who used it and when, what its state was and which interdependencies precluded (if there was a preclusion) their use at what point in time.

Certain examples enable task durations to be simulated forward and calculate the delays, if any, by resource. Simulation can be used to achieve variability. A closed form expression of variation, such as a normal distribution's mean and standard deviation, or more probably, lognormal durations, can also be consumed. Additionally, a simulation can impose exogenous variation onto a healthcare delivery system (e.g., demand, case mix, equipment and staff availability, etc.). Certain examples consider potential changes that could alter the clinical activity schedule and probabilities of handling those changes.

Certain examples consume a duration probability for a task and calculate schedule risk and transitions in schedule risk state. Patient descriptive attributes, such as weight, co-morbidities and age can be used as forecast indicators for task duration, assuming all other factors being equal (such as equipment state and availability being the same). Forecasted task durations can be changed as a function of patient attribute.

Certain examples identify that some tasks can be performed in a protocol, even if all tasks in a clinical service cannot be. Additionally, assets such as medical devices and surgical kits or people such as those who make up a surgical team have states and availabilities that can be managed with workflows, which can be prescribed. For example, an asset such as a medical device may be monitored, diagnosed and prognosticated as having a questionable calibration or forecasted to be out of a dispensed drug such as in anesthesia, at a certain time interval in the future, given the schedule of use and evolving state of that apparatus. An exact interdependency that triggers a repair or refill workflow can be specified, and that activity can be timed so as to minimize schedule impact. In another example, a surgery may be started knowing that a certain required person is at a known state of completion on a prerequisite task. Certain examples resolve "what-if" scenarios and place tasks as a granular function resolved using specific relationships between clinical services, protocols, tasks and dependent resources. A likelihood of a schedule being met is calculated as opposed to assuming everything is available if a physical time opening assumes all resources are 100% in place.

Certain examples enable dynamic what-if analysis for the current time and future, with the specificity to understand shared resource constraints, effects of certain variability, pinch points during the day for physical space, people, assets and consumables. A graphical interface enables a real time scenario calculation and feedback with the states of resources changing color, the probabilities changing and the robustness of a schedule in real time or near real-time, for example.

Figure 19:
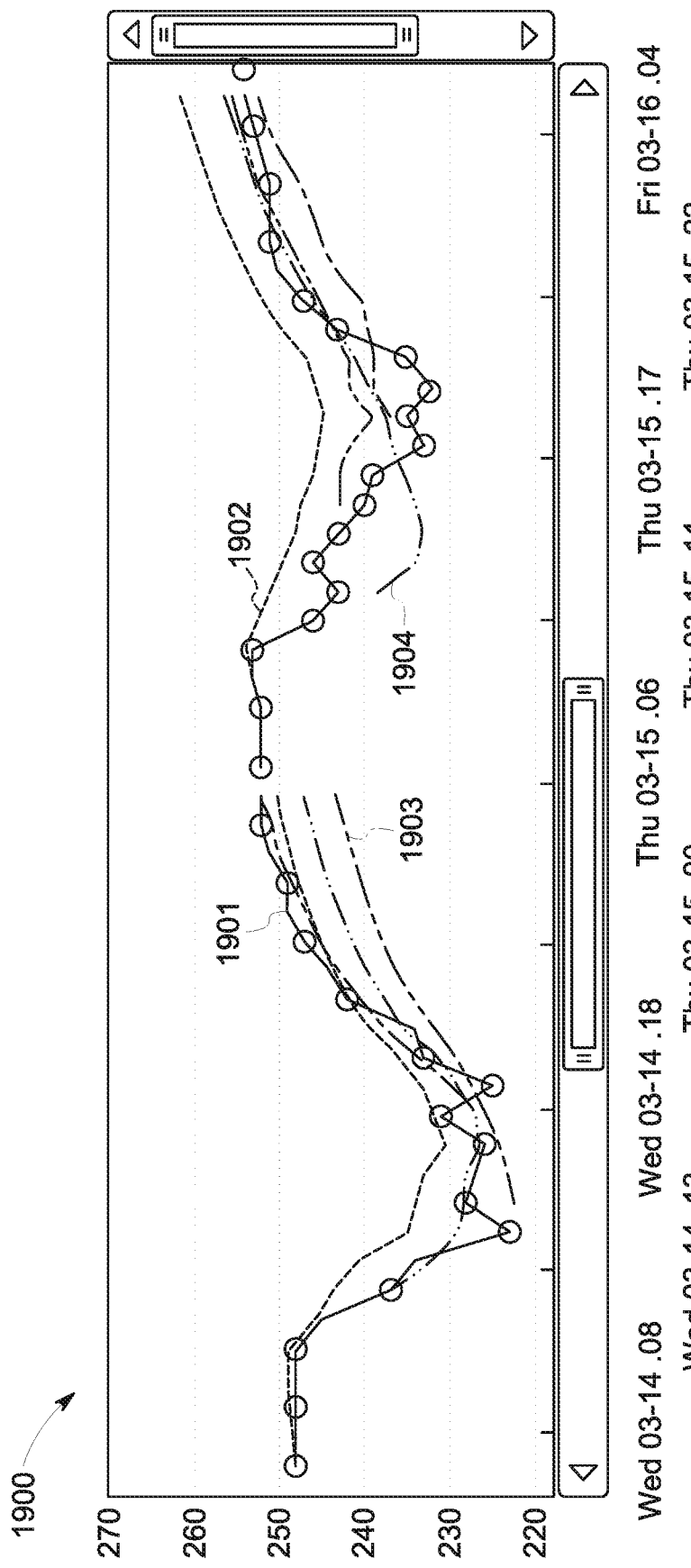
FIG. 19 shows an example visualization of simulation forecasts used in accordance with example embodiments disclosed and described herein.

FIG. 19 shows an example visualization 1900 of simulation forecasts generated from a closed loop feedback system such as the system 1800 described above. The visualization interface 1900 shows, for each of a plurality of monitored services (e.g., a medical service and a heart service in this example), a superimposition of four different simulation forecasts made starting at different times of the day (colorful and/or patterned lines 1902-1904) against the reality (black line 1901) after that reality unfolds, to retroactively verify the forecasts. That is, the remainder of the black line 1901 was not known to the simulations for X coordinates past their origin at the time those simulations were ran.

Additionally, the black line 1901 (alone or in conjunction with a zone or cone of future probability around it) may be used to represent an as-is future (e.g., if no mitigation action is taken in an attempt to get the workflow back on track). The additional lines 1902-1904 (alone or in conjunction with a surround prediction-interval cone or zone) can provide proposed alternatives to judge a probabilistic predicted impact of a mitigation strategy on a desired goal, objective, metric, performance indicator, etc. Based on the visualization 1900, projected outcomes can be reviewed, and an option can be selected (e.g., based on a desired risk/reward balance). In some examples, selection of an option via the visualization 1900 can trigger a change in workflow (e.g., provided as proactive decision support back to a hospital system).

Thus, certain examples provide systems and methods to determine schedule risk state and optimize or otherwise improve state transition set points for schedule risk management. Certain examples augment decision support to alert and/or correct for changes in schedule risk state to help ensure objective(s) and setpoint(s) are met. Certain examples dynamically and automatically monitor schedule progress over a time period and trigger alerts to generate awareness and/or actions to execute workflows to correct for an increase in schedule risk impacting operations.

Certain examples apply optimization and/or other improvement for schedule risk.

Rather than using point estimates and averages or relying on a calendar to reconcile interdependencies, certain examples utilize probabilities, probability density functions, and a cumulative distribution function to identify and accommodate schedule risk and define setpoints for risk state transition.

Certain examples provide an interactive decision support system in which stakeholders can reconcile a day's constraints collaboratively by scenario playing "what-if" ideas to reduce schedule risk. Certain examples automatically set upper and lower specification limits (USL and LSL) to determine schedule risk state (e.g., ok, warning, in high danger of late completion, etc.).

Certain examples automatically set points at which schedule risk state transitions occur as a function of one or more operational aims of an organization. In an example, an optimizer sets state transitions automatically to achieve one or more global objectives defined for a clinic, office, department, hospital, specialty, etc.

Risk state definition and monitoring for transition enables probabilistic scheduling to have escalation automation and a global (e.g., organizational or other higher-level) optimization capability. This enables more workflows to be kept on schedule at a minimum and optimizes departmental level tradeoffs at a maximum.

As a result of automatically setting the schedule alarm points, specific workflows can be triggered that optimize globally—such as targeted notifications to people and for resources that, if left unmanaged, would enable the formation of a future bottleneck or conversely, enable too much underutilized capacity.

Certain examples provide a multi-criteria stochastic optimization loop that wraps around scheduling and schedule monitoring methods and systems to enable calculation of schedule interdependencies and probabilities. Certain examples set schedule risk state transition definitions according to one or more criterion. Examples of criteria include finishing scheduled tasks at a certain probability, triggering workflow rules such as auto-moving surgeries or ancillary services that increase (or decrease) probability of completion, staffing decision support (overtime, re-assign, call off, etc.), service level agreement management, interdepartmental scheduling input/output, budgeting, service line or case prioritization, etc.

Schedule risk determination rather than a "yes/no" feasibility is valuable in the clinical workflow context. While related systems and methods calculate schedule risk by viewing schedule interdependencies and providing proactive clinical process decision support (see, e.g., application Ser. No. 12/040,646, which is herein incorporated by reference in its entirety, certain examples improve upon prior approaches to set when a schedule transitions in total or in a given interval, when the risk transitions from acceptable, warning or unacceptable. Certain examples automatically (and with optimization) set state transitions for schedule risk designation.

Certain examples provide systems and methods for using probabilities to schedule and modify schedules and clinical processes in healthcare delivery. Certain examples provide systems and methods to calculate the probability that a scheduled task will start at given a time using CPM and PERT with assumptions derived from an active process feedback and probabilistic historical task durations. Certain examples provide systems and methods to calculate the probability that a scheduled task will end at given a time using CPM and PERT with assumptions derived from an active process feedback and probabilistic historical task durations. Certain examples provide systems and methods to calculate the probability that a whole or any part of a schedule will start and/or complete as scheduled and/or a given time(s) using CPM and PERT with assumptions derived from an active process feedback and probabilistic historical task durations.

Certain examples provide systems and methods to calculate the time that scheduled task will start given a desired probability of a start occurring using CPM and PERT in a simulation or static mode drawing upon assumptions derived from an active process feedback and probabilistic historical task durations. Certain examples provide systems and methods to calculate the time that a scheduled task will end given a probability of an end occurring using CPM and PERT with assumptions derived from an active process feedback and probabilistic historical task durations.

Certain examples provide systems and methods to calculate the probability of meeting tasks in a schedule of healthcare clinical processes using the critical path method (CPM) to identify tasks and interdependencies that will be impacted by any other task or resource at any time in the schedule.

Certain examples provide systems and methods of using probabilistic durations with the CPM and or PERT methods to calculate probabilities of scheduled task starts of finishes and predicent and anticent tasks or resources (people, assets and information) in healthcare clinical processes.

Certain examples provide systems and methods to use CPM or PERT to calculate slack time for resources in the active processes of healthcare delivery by embedding the algorithms of these methods into a computerized information and decisioning system which actively takes in process and related information, calculates the algorithms and provides active process decision support or automation at one or a multiple of locations.

Certain examples provide systems and methods to warn process stakeholders of a deviation from schedule that will under or over utilize capacity of a process in advance of the scheduled time for that process or resource using CPM and PERT with assumptions derived from an active process feedback and probabilistic historical task durations and will feed forward capacity ramifications to process stakeholders who make decisions to add or drop surgical cases or manage beds, transportation and physical assets.

Certain examples provide systems and methods to incorporate dynamically updated probability distributions which benefit from the historical and current actual process durations at one or a plurality of hospitals such that the assumptions gain ever more precision where observations at one hospital may be too infrequent into the CPM/PERT based logic rather than a static probability assumptions to calculate probabilities of scheduled task starts or finishes for tasks or resources (People, assets and information) in healthcare clinical processes.

Certain examples provide systems and methods for illuminating various states of the schedule with visual, audible, tactile, numerical or shape (or any combination there of) context relative to the degree of impact if certain tasks are not done or resources made available.

Certain examples provide systems and methods to identify root cause of actual and likely schedule variation by a decision logic tree incorporating schedule risk calculated from a cumulative probability density function or closed form approximation and active process status feedback combined with Gantt, CPM or PERT algorithms in healthcare delivery processes.

Certain examples provide systems and methods to identify what resource(s) to focus on to change the schedule using a decision logic tree incorporating schedule risk calculated from a cumulative probability density function or closed form approximation and active process status feedback combined with Gantt, CPM or PERT algorithms in healthcare delivery processes.

Certain examples include systems and methods providing use in combination of discrete event, agent based, continuous or system dynamics simulation or Monte Carlo simulation integrated with PERT and CPM in healthcare related processes to simulate "what if" scenarios, calculate schedule risk, find feasible process solutions, replay events of historical record in an emulation and as a transfer function that can be called from an optimization.

Certain examples include systems and methods providing use of agent based simulation integrated with PERT and CPM in healthcare related processes to simulate "what if" scenarios, calculate schedule risk, find feasible process solutions, replay events of historical record in an emulation and as a transfer function that can be called from an optimization.

Certain examples include systems and methods providing use of continuous or System Dynamics simulation integrated with PERT and CPM in healthcare related processes to simulate "what if" scenarios, calculate schedule risk, find feasible process solutions, replay events of historical record in an emulation and as a transfer function that can be called from an optimization.

Certain examples include systems and methods providing use of Monte Carlo simulation integrated with PERT and CPM in healthcare related processes to simulate "what if" scenarios, calculate schedule risk, find feasible process solutions, replay events of historical record in an emulation and as a transfer function that can be called from an optimization.

Certain examples include systems and methods providing use of singularly and/or in combination of discrete event, agent based, continuous or system dynamics and Monte Carlo simulation integrated with PERT and CPM in inter-related healthcare delivery or support processes in and amongst departments or hospital networks in a region to simulate "what if" scenarios, calculate schedule risk, find feasible process solutions, replay events of historical record in an emulation and as a transfer function that can be called from an optimization.

Certain examples provide systems and methods to replay "what was" emulations of actual processes at one or a plurality of hospitals for individual or team learning with an interactive user interface or structured command.

Certain examples provide systems and methods utilizing "what was" emulation or simulation for activity based costing estimates, checks, validations, re-engineering or justification. Certain examples provide systems and methods utilizing "what was" emulation or simulation for billing. Certain examples provide systems and methods to replay "what was" for team, peer and operational learning. Certain examples provide systems and methods utilizing "what was" historical records to train decision support algorithms that include case-based reasoning, rule-based, fuzzy logic, example-based evidentiary reasoning, neural net, regressive, heuristic or other artificial intelligence based algorithms.

Certain examples provide systems and methods utilizing "what was" to calibrate simulation model(s). Certain examples provide systems and methods utilizing "what was" for process study, analysis, peer review, re-engineering, best practice sharing and benchmarking.

Certain examples provide systems and methods utilizing the planned schedule and comparing it live against "what-is" for process study, analysis, peer review, re-engineering, best practice sharing, decision support and benchmarking.

Certain examples provide systems and methods utilizing "what was" for case cart and equipment, assets and resources preferences and decision support process study, analysis, peer review, re-engineering, best practice sharing, decision support and benchmarking.

Certain examples provide systems and methods to provide decision support as to where best, given one or more process objectives, to add and insert task(s).

Certain examples provide systems and methods to provide decision support as to what tasks to drop and resources to release from specific tasks in order to best meet objective(s) of the process when the schedule changes for any reason.

Certain examples provide systems and methods to adjust blocks of dynamically allocated time.

Certain examples provide systems and methods to dynamically adjust upper and lower specification limits for various alerts.

Certain examples provide systems and methods to call clinical protocol into the CPM structure for schedule monitoring.

Certain examples provide a capability to create an exception report for schedule and protocol mismatch.

Certain examples provide an ability to configure protocol and schedule mismatch presentation where they are matched, with schedules greater than protocol, protocol greater than schedule as an exception.

Certain examples provide a capability to integrate equipment, biometrical or personal information into a schedule in order to determine impact on the schedule Certain examples provide an ability to use optical and/or RFID with dynamic data from an EMR to assess/forecast the status or degree of task completeness and resources utilization.

Certain examples provide an ability to incorporate equipment prognostics into the schedule risk calculation(s).

Certain examples provide an ability to incorporate PDF frequency histograms, look-up tables & cumulative probability distributions for procedure duration, staff availability and skill, equipment reliability into the CPM and simulation method assumptions.

Certain examples provide an ability to simulate forward to explore feasible and more robust or flexible alternative schedules that satisfy one or more objectives.

Certain examples provide coupling of linear programming and/or stochastic optimization to trade off process objectives for one or more process objectives.

Certain examples provide systems and methods to simulate forward to explore alternative schedules using CPM and PERT task and asset relationship methods where rule based or simulations utilizing agent based, discrete event, Monte Carlo or continuous differential methods are used to forecast assets of the process behavior.

Certain examples provide an ability to forecast the long term relationships between investment in resources, staff, information, healthcare providers with the change in capability and the attraction of more patients with resulting revenues.

Certain examples provide an ability to use 'what ifs' to plan equipment and surgical inventory logistics.

Certain examples provide an ability to use analytical workflow in coordinating the analytical task in an automated and semi-automated fashion.

Certain examples provide an ability to summarize the state of the process in either actual time, simulated forward or the emulated historical record and provide a visual indicator such as red/yellow/green, shapes, happy faces, or other audible and visual representation.

Certain examples provide an ability to use probabilistic setpoints to summarize the state of the schedule performance or risk in either actual time, simulated forward or the emulated historical record.

Several examples are described above with reference to drawings. These drawings illustrate certain details of specific examples that implement the systems and methods and programs of the presently described technology. However, describing the disclosed technology with drawings should not be construed as imposing on the invention any limitations associated with features shown in the drawings. The present invention contemplates methods, systems and program products on any machine-readable media for accomplishing its operations. As noted above, the embodiments of the present invention may be implemented using an existing computer processor, or by a special purpose computer processor incorporated for this or another purpose or by a hardwired system.

As noted above, embodiments within the scope of the present invention include program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the invention are described in the general context of method steps which may be implemented in one embodiment by a program product including machine-executable instructions, such as program code, for example in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represents examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

Figure 20:
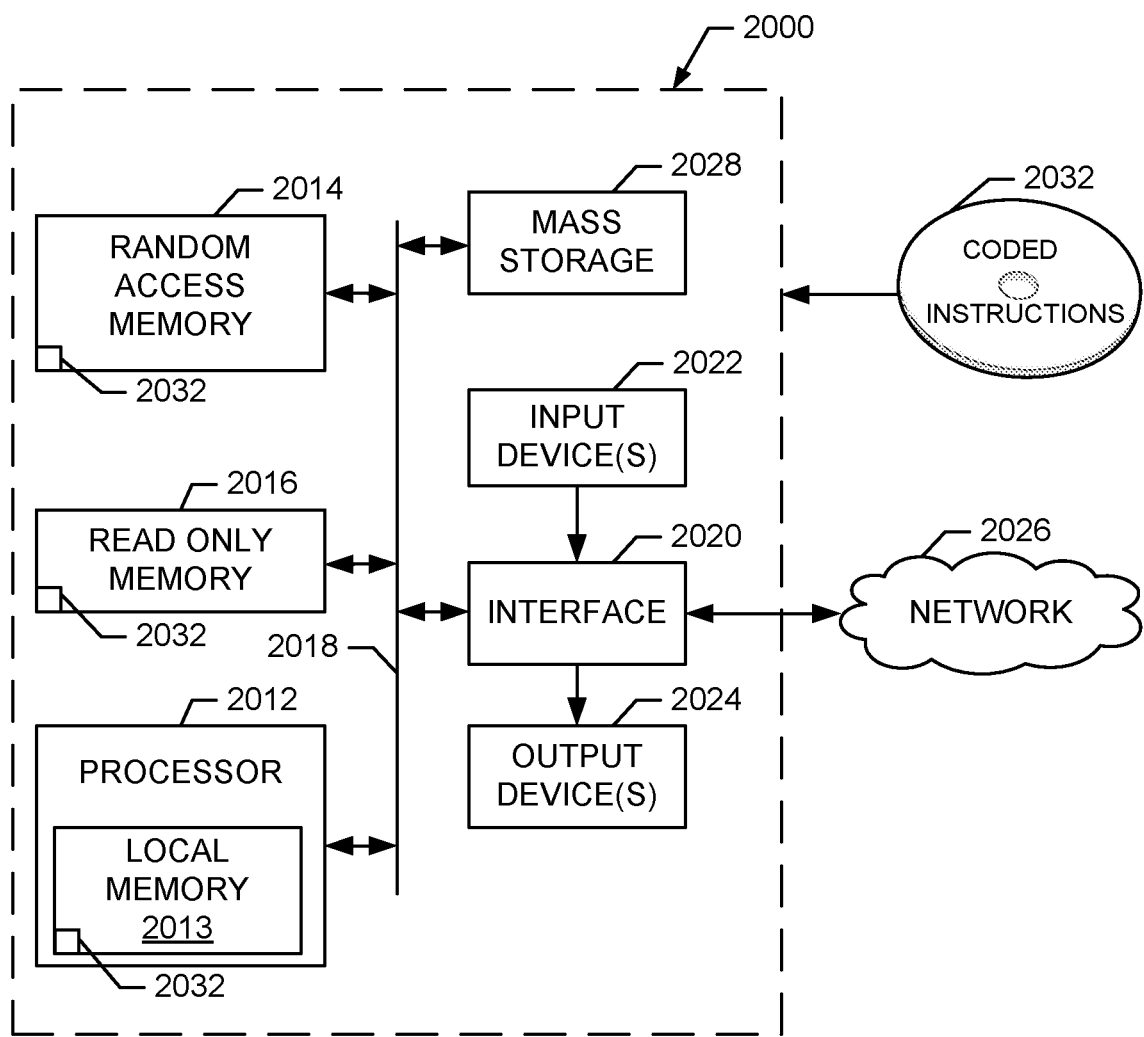
FIG. 20 shows a block diagram of an example processor system that can be used to implement systems and methods described herein.

For example, FIG. 20 is a block diagram of an example processor platform 2000 capable of executing instructions to implement the systems and methods disclosed and described herein. The processor platform 2000 can be, for example, a server, a personal computer, a mobile device (e.g., a cell phone, a smart phone, a tablet such as an IPAD™) a personal digital assistant (PDA), an Internet appliance, or any other type of computing device.

The processor platform 2000 of the illustrated example includes a processor 2012. The processor 2012 of the illustrated example is hardware. For example, the processor 2012 can be implemented by one or more integrated circuits, logic circuits, microprocessors or controllers from any desired family or manufacturer.

The processor 2012 of the illustrated example includes a local memory 2013 (e.g., a cache). The processor 2012 of the illustrated example is in communication with a main memory including a volatile memory 2014 and a non-volatile memory 2016 via a bus 2018. The volatile memory 2014 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 2016 can be implemented by flash memory and/or any other desired type of memory device. Access to the main memory 2014, 2016 is controlled by a memory controller.

The processor platform 2000 of the illustrated example also includes an interface circuit 2020. The interface circuit 2020 can be implemented by any type of interface standard, such as an Ethernet interface, a universal serial bus (USB), and/or a PCI express interface.

In the illustrated example, one or more input devices 2022 are connected to the interface circuit 2020. The input device(s) 2022 permit(s) a user to enter data and commands into the processor 2012. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 2024 are also connected to the interface circuit 2020 of the illustrated example. The output devices 2024 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 2020 of the illustrated example, thus, typically includes a graphics driver card, a graphics driver chip or a graphics driver processor.

The interface circuit 2020 of the illustrated example also includes a communication device such as a transmitter, a receiver, a transceiver, a modem and/or network interface card to facilitate exchange of data with external machines (e.g., computing devices of any kind) via a network 2026 (e.g., an Ethernet connection, a digital subscriber line (DSL), a telephone line, coaxial cable, a cellular telephone system, etc.).

The processor platform 2000 of the illustrated example also includes one or more mass storage devices 2028 for storing software and/or data. Examples of such mass storage devices 2028 include floppy disk drives, hard drive disks, compact disk drives, Blu-ray disk drives, RAID systems, and digital versatile disk (DVD) drives.

The coded instructions 2032 (e.g., from FIGS. 17, 18, etc.) can be stored in the mass storage device 2028, in the volatile memory 2014, in the non-volatile memory 2016, and/or on a removable tangible computer readable storage medium such as a CD or DVD.

As used herein, "tangible computer readable storage medium" and "tangible machine readable storage medium" are used interchangeably. As used herein, the term "non-transitory computer readable medium" is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

Those skilled in the art will appreciate that the embodiments disclosed herein may be applied to the formation of any clinical scheduling/planning system. Certain features of the embodiments of the claimed subject matter have been illustrated as described herein; however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

The invention claimed is:

1. A system comprising:
   at least one memory including instructions; and
   at least one processor configured to execute the instructions to at least:
   calculate a cumulative distribution function for a cumulative duration of a plurality of tasks in a schedule to execute a healthcare protocol using a device based on probability density functions associated with task durations for the tasks;
   define, based on the cumulative distribution function, a plurality of schedule risk states for the healthcare protocol, each schedule risk state defined by an upper specification limit and a lower specification limit, the upper specification limit and lower specification limit represented by setpoints establishing a transition between schedule risk states in the plurality of schedule risk states, wherein the setpoints are set based on at least one objective for execution by the device;
   monitor execution of the tasks by the device to identify a transition in schedule risk state according to at least one setpoint;
   trigger a workflow action executed by the device based on the identified transition; and
   adjust at least one of the plurality of schedule risk states for a next execution of tasks by moving at least one setpoint based on the identified transition and the at least one objective for execution by the device.

2. The system of claim 1, wherein the at least one objective includes a service level objective.

3. The system of claim 1, wherein the at least one objective includes at least one of an operating margin, a clinical capability, or staff burnout.

4. The system of claim 1, wherein at least one schedule risk state is to be adjusted based on a simulation.

5. The system of claim 1, wherein at least one schedule risk state is to be adjusted based on feedback.

6. The system of claim 1, wherein at least one schedule risk state is to be adjusted based on the workflow action.

7. The system of claim 1, wherein the lower specification limit indicates a minimum probability threshold of completing a task within an allocated time, and wherein the upper specification limit represents an adjustable surplus probability over an expected duration probability for the task.

8. At least one non-transitory computer-readable storage medium comprising instructions for execution by at least one processor, the instructions, when executed, to cause the at least one processor to at least:
   calculate a cumulative distribution function for a cumulative duration of a plurality of tasks in a schedule to execute a healthcare protocol using a device based on probability density functions associated with task durations for the tasks;
   define, based on the cumulative distribution function, a plurality of schedule risk states for the healthcare protocol, each schedule risk state defined by an upper specification limit and a lower specification limit, the upper specification limit and lower specification limit represented by setpoints establishing a transition between schedule risk states in the plurality of schedule risk states, wherein the setpoints are set based on at least one objective for execution by the device;
   monitor execution of the tasks by the device to identify a transition in schedule risk state according to at least one setpoint;
   trigger a workflow action executed by the device based on the identified transition; and
   adjust at least one of the plurality of schedule risk states for a next execution of tasks by moving at least one setpoint based on the identified transition and the at least one objective for execution by the device.

9. The at least one non-transitory computer-readable storage medium of claim 8, wherein the at least one objective includes a service level objective.

10. The at least one non-transitory computer-readable storage medium of claim 8, wherein the at least one objective includes at least one of an operating margin, a clinical capability, or staff burnout.

11. The at least one non-transitory computer-readable storage medium of claim 8, wherein at least one schedule risk state is to be adjusted based on a simulation.

12. The at least one non-transitory computer-readable storage medium of claim 8, wherein at least one schedule risk state is to be adjusted based on feedback.

13. The at least one non-transitory computer-readable storage medium of claim 8, wherein at least one schedule risk state is to be adjusted based on the workflow action.

14. The at least one non-transitory computer-readable storage medium of claim 8, wherein the lower specification limit indicates a minimum probability threshold of completing a task within an allocated time, and wherein the upper specification limit represents an adjustable surplus probability over an expected duration probability for the task.

15. A processor-implemented method comprising:
calculating, by executing an instruction using the processor, a cumulative distribution function for a cumulative duration of a plurality of tasks in a schedule to execute a healthcare protocol using a device based on probability density functions associated with task durations for the tasks;
defining, based on the cumulative distribution function by executing an instruction using the processor, a plurality of schedule risk states for the healthcare protocol, each schedule risk state defined by an upper specification limit and a lower specification limit, the upper specification limit and lower specification limit represented by setpoints establishing a transition between schedule risk states in the plurality of schedule risk states, wherein the setpoints are set based on at least one objective for execution by the device;
monitoring, by executing an instruction using the processor, execution of the tasks by the device to identify a transition in schedule risk state according to at least one setpoint;
triggering, by executing an instruction using the processor, a workflow action executed by the device based on the identified transition; and
adjusting, by executing an instruction using the processor, at least one of the plurality of schedule risk states for a next execution of tasks by moving at least one setpoint based on the identified transition and the at least one objective for execution by the device.

16. The method of claim 15, wherein the at least one objective includes at least one of a service level objective, an operating margin, a clinical capability, or staff burnout.

17. The method of claim 15, wherein at least one schedule risk state is to be adjusted based on a simulation.

18. The method of claim 15, wherein at least one schedule risk state is to be adjusted based on feedback.

19. The method of claim 15, wherein at least one schedule risk state is to be adjusted based on the workflow action.

20. The method of claim 15, wherein the lower specification limit indicates a minimum probability threshold of completing a task within an allocated time, and wherein the upper specification limit represents an adjustable surplus probability over an expected duration probability for the task.

* * * * *